(12) United States Patent
Cunningham et al.

(10) Patent No.: US 7,879,360 B2
(45) Date of Patent: Feb. 1, 2011

(54) NANOPARTICULATE COMPOSITIONS HAVING A PEPTIDE AS A SURFACE STABILIZER

(75) Inventors: James Cunningham, Malvern, PA (US); Elaine Merisko Liversidge, West Chester, PA (US)

(73) Assignee: Elan Pharma International, Ltd., Athlone, County Westmeath (IE)

( * ) Notice: Subject to any disclaimer, the term of this patent is extended or adjusted under 35 U.S.C. 154(b) by 1205 days.

(21) Appl. No.: 10/978,695

(22) Filed: Nov. 2, 2004

(65) Prior Publication Data

US 2005/0238725 A1      Oct. 27, 2005

Related U.S. Application Data

(60) Provisional application No. 60/517,106, filed on Nov. 5, 2003.

(51) Int. Cl.
*A61K 9/14* (2006.01)
*A61K 9/16* (2006.01)
*A61K 9/20* (2006.01)
*A61K 9/48* (2006.01)

(52) U.S. Cl. ................. 424/489; 424/451; 424/464; 424/490

(58) Field of Classification Search ................. None
See application file for complete search history.

(56) References Cited

U.S. PATENT DOCUMENTS

| | | |
|---|---|---|
| 4,783,484 A | 11/1988 | Violante et al. |
| 4,826,689 A | 5/1989 | Violanto et al. |
| 4,997,454 A | 3/1991 | Violante et al. |
| 5,145,684 A | 9/1992 | Liversidge et al. |
| 5,298,262 A | 3/1994 | Na et al. |
| 5,302,401 A | 4/1994 | Liversidge et al. |
| 5,318,767 A | 6/1994 | Liversidge et al. |
| 5,326,552 A | 7/1994 | Na et al. |
| 5,328,404 A | 7/1994 | Bacon |
| 5,336,507 A | 8/1994 | Na et al. |
| 5,340,564 A | 8/1994 | Illig et al. |
| 5,346,702 A | 9/1994 | Na et al. |
| 5,349,957 A | 9/1994 | Yudelson |
| 5,352,459 A | 10/1994 | Hollister et al. |
| 5,399,363 A | 3/1995 | Liversidge et al. |
| 5,401,492 A | 3/1995 | Kellar et al. |
| 5,429,824 A | 7/1995 | June |
| 5,447,710 A | 9/1995 | Na et al. |
| 5,451,393 A | 9/1995 | Liversidge et al. |
| 5,466,440 A | 11/1995 | Ruddy et al. |
| 5,470,583 A | 11/1995 | Na et al. |
| 5,472,683 A | 12/1995 | Illig |
| 5,494,683 A | 2/1996 | Liversidge et al. |
| 5,500,204 A | 3/1996 | Osifo |
| 5,510,118 A | 4/1996 | Bosch et al. |
| 5,518,187 A | 5/1996 | Bruno et al. |
| 5,518,738 A | 5/1996 | Eickhoff et al. |
| 5,521,218 A | 5/1996 | Osifo |
| 5,525,328 A | 6/1996 | Bacon et al. |
| 5,534,270 A | 7/1996 | De Castro |
| 5,543,133 A | 8/1996 | Swanson et al. |
| 5,552,160 A | 9/1996 | Liversidge et al. |
| 5,560,931 A | 10/1996 | Eickhoff et al. |
| 5,560,932 A | 10/1996 | Bagchi et al. |
| 5,565,188 A | 10/1996 | Wong et al. |
| 5,569,448 A | 10/1996 | Wong et al. |
| 5,571,536 A | 11/1996 | Eickhoff et al. |
| 5,573,749 A | 11/1996 | Illig |
| 5,573,750 A | 11/1996 | Singh |
| 5,573,783 A | 11/1996 | Desieno et al. |
| 5,580,579 A | 12/1996 | Ruddy et al. |
| 5,585,108 A | 12/1996 | Ruddy et al. |
| 5,587,143 A | 12/1996 | Wong |
| 5,591,456 A | 1/1997 | Franson et al. |
| 5,593,657 A | 1/1997 | Ruddy et al. |
| 5,622,938 A | 4/1997 | Wong |
| 5,628,981 A | 5/1997 | Liversidge et al. |
| 5,643,552 A | 7/1997 | Illig |
| 5,662,883 A | 9/1997 | Bagchi et al. |
| 5,665,331 A | 9/1997 | Bagchi et al. |
| 5,718,388 A | 2/1998 | Czekai et al. |
| 5,718,919 A | 2/1998 | Ruddy et al. |
| 5,741,522 A | 4/1998 | Violante et al. |
| 5,747,001 A | 5/1998 | Wiedmann et al. |
| 5,776,496 A | 7/1998 | Violante et al. |
| 5,834,025 A | 11/1998 | De Garavilla et al. |
| 5,862,999 A | 1/1999 | Czekai et al. |

(Continued)

FOREIGN PATENT DOCUMENTS

WO    WO 02/098565 A1    12/2002

(Continued)

OTHER PUBLICATIONS

Stryer, *Biochemistry*, 3rd edition, pp. 1-41 (W.H. Freeman & Co., NY, 1988).

*Primary Examiner*—S. Tran
(74) *Attorney, Agent, or Firm*—Foley & Lardner LLP

(57) ABSTRACT

The present invention is directed to nanoparticulate active agent compositions comprising at least one peptide as a surface stabilizer. Also encompassed by the invention are pharmaceutical compositions comprising a nanoparticulate active agent composition of the invention and methods of making and using such nanoparticulate and pharmaceutical compositions.

25 Claims, 3 Drawing Sheets

U.S. PATENT DOCUMENTS

| | | | |
|---|---|---|---|
| 6,045,829 | A | 4/2000 | Liversidge et al. |
| 6,068,858 | A | 5/2000 | Liversidge et al. |
| 6,153,225 | A | 11/2000 | Lee et al. |
| 6,165,506 | A | 12/2000 | Jain et al. |
| 6,221,400 | B1 | 4/2001 | Liversidge et al. |
| 6,264,922 | B1 | 7/2001 | Wood et al. |
| 6,267,989 | B1 | 7/2001 | Liversidge et al. |
| 6,270,806 | B1 | 8/2001 | Liversidge et al. |
| 6,316,029 | B1 | 11/2001 | Jain et al. |
| 6,375,986 | B1 | 4/2002 | Ryde et al. |
| 6,428,814 | B1 | 8/2002 | Bosch |
| 6,431,478 | B1 | 8/2002 | Reed et al. |
| 6,432,381 | B2 | 8/2002 | Liversidge et al. |
| 6,582,285 | B2 | 6/2003 | Czekai et al. |
| 6,592,903 | B2 | 7/2003 | Ryde et al. |
| 6,656,504 | B1 | 12/2003 | Bosch et al. |
| 6,742,734 | B2 | 6/2004 | Reed et al. |
| 6,745,962 | B2 | 6/2004 | Reed et al. |
| 2001/0006823 | A1 * | 7/2001 | Yoshimura et al. .......... 436/518 |
| 2002/0012675 | A1 | 1/2002 | Jain et al. |
| 2004/0018242 | A1 * | 1/2004 | Cunningham et al. ....... 424/489 |

FOREIGN PATENT DOCUMENTS

| | | |
|---|---|---|
| WO | WO 03/066021 A2 | 8/2003 |
| WO | WO 03/080024 A2 | 10/2003 |
| WO | WO 03/080027 A1 * | 10/2003 |
| WO | WO 03/086354 A1 | 10/2003 |
| WO | WO 03/094894 A1 | 11/2003 |

* cited by examiner

A

B

NANOPARTICULATE COMPOSITIONS HAVING A PEPTIDE AS A SURFACE STABILIZER

FIELD OF THE INVENTION

The present invention is directed to nanoparticulate active agent compositions having a peptide adsorbed onto or associated with the surface of the active agent as a surface stabilizer, and methods of making and using such compositions.

BACKGROUND OF THE INVENTION

Nanoparticulate active agent compositions, first described in U.S. Pat. No. 5,145,684 ("the '684 patent"), are particles consisting of a poorly soluble therapeutic or diagnostic agent having adsorbed onto, or associated with, the surface thereof a non-crosslinked surface stabilizer. The '684 patent describes the use of a variety of surface stabilizers for nanoparticulate compositions. The use of a peptide as a surface stabilizer for nanoparticulate active agent compositions is not described by the '684 patent.

The '684 patent describes a method of screening active agents to identify useful surface stabilizers that enable the production of a nanoparticulate composition. Not all surface stabilizers will function to produce a stable, non-agglomerated nanoparticulate composition for all active agents. Moreover, known surface stabilizers may be unable to produce a stable, non-agglomerated nanoparticulate composition for certain active agents. Thus, there is a need in the art to identify new surface stabilizers useful in making nanoparticulate active agent compositions. Additionally, such new surface stabilizers may have superior properties over prior known surface stabilizers.

Methods of making nanoparticulate active agent compositions are described, for example, in U.S. Pat. Nos. 5,518,187 and 5,862,999, both for "Method of Grinding Pharmaceutical Substances;" U.S. Pat. No. 5,718,388, for "Continuous Method of Grinding Pharmaceutical Substances;" and U.S. Pat. No. 5,510,118 for "Process of Preparing Therapeutic Compositions Containing Nanoparticles."

Nanoparticulate active agent compositions are also described, for example, in U.S. Pat. No. 5,298,262 for "Use of Ionic Cloud Point Modifiers to Prevent Particle Aggregation During Sterilization;" U.S. Pat. No. 5,302,401 for "Method to Reduce Particle Size Growth During Lyophilization;" U.S. Pat. No. 5,318,767 for "X-Ray Contrast Compositions Useful in Medical Imaging;" U.S. Pat. No. 5,326,552 for "Novel Formulation For Nanoparticulate X-Ray Blood Pool Contrast Agents Using High Molecular Weight Non-ionic Surfactants;" U.S. Pat. No. 5,328,404 for "Method of X-Ray Imaging Using Iodinated Aromatic Propanedioates;" U.S. Pat. No. 5,336,507 for "Use of Charged Phospholipids to Reduce Nanoparticle Aggregation;" U.S. Pat. No. 5,340,564 for "Formulations Comprising Olin 10-G to Prevent Particle Aggregation and Increase Stability;" U.S. Pat. No. 5,346,702 for "Use of Non-Ionic Cloud Point Modifiers to Minimize Nanoparticulate Aggregation During Sterilization;" U.S. Pat. No. 5,349,957 for "Preparation and Magnetic Properties of Very Small Magnetic-Dextran Particles;" U.S. Pat. No. 5,352,459 for "Use of Purified Surface Modifiers to Prevent Particle Aggregation During Sterilization;" U.S. Pat. Nos. 5,399,363 and 5,494,683, both for "Surface Modified Anticancer Nanoparticles;" U.S. Pat. No. 5,401,492 for "Water Insoluble Non-Magnetic Manganese Particles as Magnetic Resonance Enhancement Agents;" U.S. Pat. No. 5,429,824 for "Use of Tyloxapol as a Nanoparticulate Stabilizer;" U.S. Pat. No. 5,447,710 for "Method for Making Nanoparticulate X-Ray Blood Pool Contrast Agents Using High Molecular Weight Non-ionic Surfactants;" U.S. Pat. No. 5,451,393 for "X-Ray Contrast Compositions Useful in Medical Imaging;" U.S. Pat. No. 5,466,440 for "Formulations of Oral Gastrointestinal Diagnostic X-Ray Contrast Agents in Combination with Pharmaceutically Acceptable Clays;" U.S. Pat. No. 5,470,583 for "Method of Preparing Nanoparticle Compositions Containing Charged Phospholipids to Reduce Aggregation;" U.S. Pat. No. 5,472,683 for "Nanoparticulate Diagnostic Mixed Carbamic Anhydrides as X-Ray Contrast Agents for Blood Pool and Lymphatic System Imaging;" U.S. Pat. No. 5,500,204 for "Nanoparticulate Diagnostic Dimers as X-Ray Contrast Agents for Blood Pool and Lymphatic System Imaging;" U.S. Pat. No. 5,518,738 for "Nanoparticulate NSAID Formulations;" U.S. Pat. No. 5,521,218 for "Nanoparticulate Iododipamide Derivatives for Use as X-Ray Contrast Agents;" U.S. Pat. No. 5,525,328 for "Nanoparticulate Diagnostic Diatrizoxy Ester X-Ray Contrast Agents for Blood Pool and Lymphatic System Imaging;" U.S. Pat. No. 5,543,133 for "Process of Preparing X-Ray Contrast Compositions Containing Nanoparticles;" U.S. Pat. No. 5,552,160 for "Surface Modified NSAID Nanoparticles;" U.S. Pat. No. 5,560,931 for "Formulations of Compounds as Nanoparticulate Dispersions in Digestible Oils or Fatty Acids;" U.S. Pat. No. 5,565,188 for "Polyalkylene Block Copolymers as Surface Modifiers for Nanoparticles;" U.S. Pat. No. 5,569,448 for "Sulfated Non-ionic Block Copolymer Surfactant as Stabilizer Coatings for Nanoparticle Compositions;" U.S. Pat. No. 5,571,536 for "Formulations of Compounds as Nanoparticulate Dispersions in Digestible Oils or Fatty Acids;" U.S. Pat. No. 5,573,749 for "Nanoparticulate Diagnostic Mixed Carboxylic Anydrides as X-Ray Contrast Agents for Blood Pool and Lymphatic System Imaging;" U.S. Pat. No. 5,573,750 for "Diagnostic Imaging X-Ray Contrast Agents;" U.S. Pat. No. 5,573,783 for "Redispersible Nanoparticulate Film Matrices With Protective Overcoats;" U.S. Pat. No. 5,580,579 for "Site-specific Adhesion Within the GI Tract Using Nanoparticles Stabilized by High Molecular Weight, Linear Poly(ethylene Oxide) Polymers;" U.S. Pat. No. 5,585,108 for "Formulations of Oral Gastrointestinal Therapeutic Agents in Combination with Pharmaceutically Acceptable Clays;" U.S. Pat. No. 5,587,143 for "Butylene Oxide-Ethylene Oxide Block Copolymers Surfactants as Stabilizer Coatings for Nanoparticulate Compositions;" U.S. Pat. No. 5,591,456 for "Milled Naproxen with Hydroxypropyl Cellulose as Dispersion Stabilizer;" U.S. Pat. No. 5,593,657 for "Novel Barium Salt Formulations Stabilized by Non-ionic and Anionic Stabilizers;" U.S. Pat. No. 5,622,938 for "Sugar Based Surfactant for Nanocrystals;" U.S. Pat. No. 5,628,981 for "Improved Formulations of Oral Gastrointestinal Diagnostic X-Ray Contrast Agents and Oral Gastrointestinal Therapeutic Agents;" U.S. Pat. No. 5,643,552 for "Nanoparticulate Diagnostic Mixed Carbonic Anhydrides as X-Ray Contrast Agents for Blood Pool and Lymphatic System Imaging;" U.S. Pat. No. 5,718,388 for "Continuous Method of Grinding Pharmaceutical Substances;" U.S. Pat. No. 5,718,919 for "Nanoparticles Containing the R(−)Enantiomer of Ibuprofen;" U.S. Pat. No. 5,747,001 for "Aerosols Containing Beclomethasone Nanoparticle Dispersions;" U.S. Pat. No. 5,834,025 for "Reduction of Intravenously Administered Nanoparticulate Formulation Induced Adverse Physiological Reactions;" U.S. Pat. No. 6,045,829 "Nanocrystalline Formulations of Human Immunodeficiency Virus (HIV) Protease Inhibitors Using Cellulosic Surface Stabilizers;" U.S. Pat. No. 6,068,858 for "Methods of Making Nanocrystalline Formulations of Human Immunodeficiency Virus (HIV) Protease Inhibitors Using Cellulosic Surface Stabilizers;" U.S. Pat. No. 6,153,225 for "Injectable Formulations of Nanoparticulate Naproxen;" U.S. Pat. No. 6,165,506 for "New Solid Dose Form of Nanoparticulate Naproxen;" U.S. Pat. No. 6,221,400 for "Methods of Treating Mammals Using Nanocrystalline Formulations of Human Immunodeficiency Virus (HIV) Protease Inhibitors;" U.S. Pat. No. 6,264,922 for "Nebulized Aerosols Containing Nanoparticle Dispersions;" U.S. Pat. No. 6,267,989 for "Methods for Preventing Crystal Growth and Particle Aggregation in Nanoparticle Compositions;" U.S. Pat. No. 6,270,806 for "Use of PEG-Derivatized Lipids as Surface Stabilizers for Nanoparticulate Compositions;" U.S. Pat. No. 6,316,029 for "Rapidly Disintegrating Solid Oral Dosage Form," U.S. Pat. No. 6,375,986 for "Solid Dose Nanoparticulate Compositions Comprising a Synergistic Combination of a Polymeric Surface Stabilizer and Dioctyl Sodium Sulfosuccinate," U.S. Pat. No. 6,428,814 for "Bioadhesive nanoparticulate compositions having cationic surface stabilizers;" U.S. Pat. No. 6,431,478 for "Small Scale Mill;" U.S. Pat. No. 6,432,381 for "Methods for Targeting Drug Delivery to the Upper and/or Lower Gastrointestinal Tract," U.S. Pat. No. 6,656,504 for "Nanoparticulate compositions comprising amorphous cyclosporine and methods of making and using such compositions," U.S. Pat. No. 6,582,285 for "Apparatus for Sanitary Wet Milling;" U.S. Pat. No. 6,592,903 for "Nanoparticulate Dispersions Comprising a Synergistic Combination of a Polymeric Surface Stabilizer and Dioctyl Sodium Sulfosuccinate," U.S. Pat. No. 6,742,734 for "System and Method for Milling Materials," and U.S. Pat. No. 6,745,962 for "Small Scale Mill and Method Thereof," all of which are specifically incorporated by reference. In addition, U.S. Patent Application No. 20020012675 A1, published on Jan. 31, 2002, for "Controlled Release Nanoparticulate Compositions," and WO 02/098565 for "System and Method for Milling Materials," describe nanoparticulate active agent compositions, and are specifically incorporated by reference. None of these references describe nanoparticulate active agent compositions comprising a peptide surface stabilizer.

Amorphous small particle compositions are described, for example, in U.S. Pat. No. 4,783,484 for "Particulate Composition and Use Thereof as Antimicrobial Agent;" U.S. Pat. No. 4,826,689 for "Method for Making Uniformly Sized Particles from Water-Insoluble Organic Compounds;" U.S. Pat. No. 4,997,454 for "Method for Making Uniformly-Sized Particles From Insoluble Compounds;" U.S. Pat. No. 5,741,522 for "Ultrasmall, Non-aggregated Porous Particles of Uniform Size for Entrapping Gas Bubbles Within and Methods;" and U.S. Pat. No. 5,776,496, for "Ultrasmall Porous Particles for Enhancing Ultrasound Back Scatter."

There is a need in the art for new surface stabilizers useful in preparing nanoparticulate active agent compositions. The present invention satisfies this need.

SUMMARY OF THE INVENTION

The present invention is directed to nanoparticulate compositions comprising at least one active agent and at least one peptide as a surface stabilizer adsorbed on to, or associated with, the surface of the active agent.

Another aspect of the invention is directed to pharmaceutical compositions comprising a nanoparticulate active agent composition of the invention. The pharmaceutical compositions preferably comprise at least one active agent, at least one peptide, and a pharmaceutically acceptable carrier, as well as any desired excipients.

In yet another embodiment, the invention is directed to bioadhesive nanoparticulate active agent compositions comprising at least one cationic peptide as a surface stabilizer, or at least one non-cationic peptide surface stabilizer in combination with at least one secondary cationic surface stabilizer. Such compositions can coat the gut, or the desired site of application, and be retained for a period of time, thereby increasing the efficacy of the active agent as well as eliminating or decreasing the frequency of dosing.

This invention further discloses a method of making a nanoparticulate active agent composition having a peptide surface stabilizer adsorbed on or associated with the surface of the active agent. Such a method comprises contacting an active agent with at least one peptide for a time and under conditions sufficient to provide a Nanoparticle active agent/peptide composition. The peptide surface stabilizer can be contacted with the active agent either before, preferably during, or after size reduction of the active agent.

The present invention is further directed to a method of treatment comprising administering to a mammal a therapeutically effective amount of a nanoparticulate active agent/peptide composition according to the invention.

Both the foregoing general description and the following detailed description are exemplary and explanatory and are intended to provide further explanation of the invention as claimed. Other objects, advantages, and novel features will be readily apparent to those skilled in the art from the following detailed description of the invention.

DETAILED DESCRIPTION OF THE INVENTION

Figure 1:
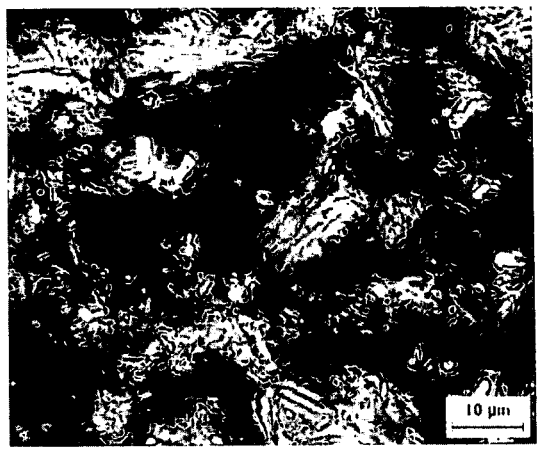
FIG. 1: Shows representative photomicrographs of nystatin crystals before (FIG. 1A) and after (FIG. 1B) milling.
Figure 1:
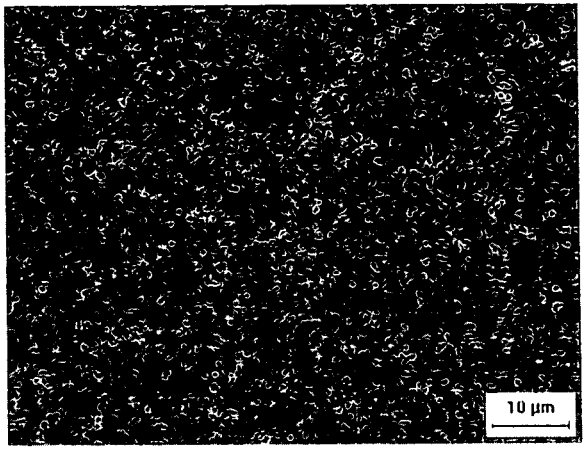

The present invention is directed to compositions comprising nanoparticulate active agents having at least one peptide as a surface stabilizer adsorbed on or associated with the surface thereof, and methods of making and using such nanoparticulate compositions.

As taught in the '684 patent, not every combination of surface stabilizer and active agent will result in a stable nanoparticulate composition. The discovery of the present invention is surprising in that peptides are biological compounds having secondary and tertiary structures which are critical to the activity of the peptide. It was surprising that such a compound could be successfully used to stabilize a nanoparticulate active agent. Moreover, it was even more surprising that milling of a peptide surface stabilizer did not change the activity or function of the peptide.

A "peptide" is defined as any compound consisting of two or more amino acids where the alpha carboxyl group of one is bound to the alpha amino group of another. A polypeptide is a long peptide chain. A protein is a large macromolecule composed of one or more polypeptide chains. In the context of the present invention, "peptide" refers to a peptide or a polypeptide, but not a protein.

A striking characteristic of peptides is that they have well-defined three dimensional structures. Peptides fold into compact structures with nominal bond lengths. The strong tendency of hydrophobic amino acid residues to flee from water drives the folding of soluble peptides.

A stretched-out or randomly arranged polypeptide chain is devoid of biological activity. This is because the function of a peptide arises from conformation, which is the three dimensional arrangement of atoms in a structure. See e.g., L. Stryer, *Biochemistry*, 3$^{rd}$ Edition, p. 1-41 (W.H. Freeman & Co., NY, 1988). Amino acid sequences are important because they specify the conformation of peptides. Id.

Peptides have several different defined structures, including a primary, secondary, and tertiary structure. The primary structure of a peptide is generally the amino acid sequence of the peptide and the location of disulfides. See e.g., L. Stryer, *Biochemistry*, 3$^{rd}$ Edition, p. 31 (W.H. Freeman & Co., NY, 1988). Secondary structure refers to the spatial arrangement of amino acid residues that are near one another in the linear sequence. Examples of these steric relationships are structures known as an alpha helix, a beta pleated sheet, and a collagen helix. Id. Tertiary structure refers to the spatial arrangement of amino acid residues in a peptide or polypeptide that are far apart in the linear sequence.

Proteins, comprising multiple polypeptide chains, also have a quaternary structure, which refers to the spatial arrangement of the polypeptide subunits and the nature of their contacts. Id.

It was very surprising that such complex compounds as peptides and polypeptides could be successfully utilized as a surface stabilizer for a nanoparticulate active agent. In addition to enabling the use of a new class of surface stabilizers for nanoparticulate active agents, this discovery is significant as the peptide surface stabilizer in the compositions of the invention may also have therapeutic or diagnostic properties. This is in contrast to prior art nanoparticulate active agent compositions, in which the surface stabilizer is generally a surfactant, which lacks such therapeutic or diagnostic properties.

The nanoparticulate active agent compositions of the invention may also offer the following advantages as compared to prior conventional or non-nanoparticulate active agent compositions: (1) faster onset of action; (2) a potential decrease in the frequency of dosing; (3) smaller doses of active agent required to obtain the same pharmacological effect; (4) increased bioavailability; (5) an increased rate of dissolution; (6) improved performance characteristics for oral, intravenous, subcutaneous, or intramuscular injection, such as higher active agent dose loading and smaller tablet or liquid dose volumes; (7) improved pharmacokinetic profiles, such as improved $T_{max}$, $C_{max}$, and AUC profiles; (8) substantially similar or bioequivalent pharmacokinetic profiles of the nanoparticulate active agent compositions when administered in the fed versus the fasted state; (9) bioadhesive active agent compositions, which can coat the gut or the desired site of application and be retained for a period of time, thereby increasing the efficacy of the active agent as well as eliminating or decreasing the frequency of dosing; (10) high redispersibility of the nanoparticulate active agent particles present in the compositions of the invention following administration; (11) the nanoparticulate active agent compositions can be formulated in a dried form which readily redisperses; (12) low viscosity liquid nanoparticulate active agent dosage forms can be made; (13) for liquid nanoparticulate active agent compositions having a low viscosity—better subject compliance due to the perception of a lighter formulation which is easier to consume and digest; (14) for liquid nanoparticulate active agent compositions having a low viscosity—ease of dispensing because one can use a cup or a syringe; (15) the nanoparticulate active agent compositions can be used in conjunction with other active agents; (16) the nanoparticulate active agent compositions can be sterile filtered; (17) the nanoparticulate active agent compositions are suitable for parenteral administration; and (18) the nanoparticulate active agent compositions do not require organic solvents or pH extremes.

A preferred dosage form of the invention is a solid dosage form, although any pharmaceutically acceptable dosage form can be utilized. Exemplary dosage forms include, but are not limited to, tablets, capsules, sachets, lozenges, powders, pills, granules, liquid dispersions, oral suspensions, gels, aerosols (including nasal and pulmonary), ointments, and creams.

The dosage form of the invention can be, for example, a fast melt dosage form, controlled release dosage form, lyophilized dosage form, delayed release dosage form, extended release dosage form, pulsatile release dosage form, mixed immediate release and controlled release dosage form, or a combination thereof.

In addition, the compositions of the invention can be formulated for any suitable administration route, such as oral, pulmonary, rectal, opthalmic, colonic, parenteral, intracisternal, intravaginal, intraperitoneal, local, buccal, nasal, or topical administration.

The present invention is described herein using several definitions, as set forth below and throughout the application.

As used herein, "about" will be understood by persons of ordinary skill in the art and will vary to some extent on the context in which it is used. If there are uses of the term which are not clear to persons of ordinary skill in the art given the context in which it is used, "about" will mean up to plus or minus 10% of the particular term.

"Conventional" or "non-nanoparticulate active agent" shall mean an active agent which is solubilized or which has an effective average particle size of greater than about 2 microns. Nanoparticulate active agents as defined herein have an effective average particle size of less than about 2 microns.

"Pharmaceutically acceptable" as used herein refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

"Pharmaceutically acceptable salts" as used herein refers to derivatives wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric, and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

"Poorly water soluble drugs" as used herein means those having a solubility of less than about 30 mg/ml, preferably less than about 20 mg/ml, preferably less than about 10 mg/ml, or preferably less than about 1 mg/ml. Such drugs tend to be eliminated from the gastrointestinal tract before being absorbed into the circulation.

As used herein with reference to stable drug particles, "stable" includes, but is not limited to, one or more of the following parameters: (1) that the active agent particles do not appreciably flocculate or agglomerate due to interparticle attractive forces, or otherwise significantly increase in particle size over time; (2) that the physical structure of the active agent particles is not altered over time, such as by conversion from an amorphous phase to crystalline phase; (3) that the active agent particles are chemically stable; and/or (4) where the active agent has not been subject to a heating step at or above the melting point of the active agent in the preparation of the nanoparticles of the invention.

"Therapeutically effective amount" as used herein with respect to an active agent dosage, shall mean that dosage that provides the specific pharmacological response for which the active agent is administered in a significant number of subjects in need of such treatment. It is emphasized that "therapeutically effective amount," administered to a particular subject in a particular instance will not always be effective in treating the diseases described herein, even though such dosage is deemed a 'therapeutically effective amount' by those skilled in the art. It is to be further understood that active agent dosages are, in particular instances, measured as oral dosages, or with reference to active agent levels as measured in blood.

I. Preferred Characteristics of the Nanoparticulate Active Agent Compositions of the Invention A. Increased Bioavailability, Frequency of Dosing, and Dosage Quantity The nanoparticulate active agent compositions of the invention, having at least one peptide as a surface stabilizer, may preferably exhibit increased bioavailability and require smaller doses as compared to prior non-nanoparticulate compositions of the same active agent administered at the same dose.

Any active agent can have adverse side effects. Thus, lower doses of an active agent that can achieve the same or better therapeutic effects as those observed with larger doses of a non-nanoparticulate composition of the same active agent are desired. Such lower doses may be realized with the nanoparticulate active agent compositions of the invention because the nanoparticulate active agent compositions may exhibit greater bioavailability as compared to non-nanoparticulate compositions of the same active agent, which means that smaller doses of the active agent are likely required to obtain the desired therapeutic effect.

The nanoparticulate active agent compositions of the invention may be administered less frequently and at lower doses, as compared to conventional non-nanoparticulate compositions of the same active agent, in dosage forms such as liquid dispersions, powders, sprays, aerosols (pulmonary and nasal), solid re-dispersable dosage forms, gels, ointments, creams, etc. of the nanoparticulate active agent. Lower dosages can be used because the small particle size of the active agent particles ensure greater absorption, and in the case of bioadhesive nanoparticulate active agent compositions, the active agent is retained at the desired site of application for a longer period of time as compared to conventional, non-nanoparticulate active agent dosage forms.

In one embodiment of the invention, the therapeutically effective amount of the nanoparticulate active agent compositions is 1/6, 1/5, 1/4, 1/3$^{rd}$, or 1/2 of the therapeutically effective amount of a non-nanoparticulate composition of the same active agent.

Such lower doses are preferred as they may decrease or eliminate adverse effects of the active agent. In addition, such lower doses decrease the cost of the dosage form and may increase patient compliance.

B. Pharmacokinetic Profiles of the Nanoparticulate Active Agent Compositions of the Invention The invention also preferably provides nanoparticulate active agent compositions, having at least one peptide as a surface stabilizer, and having a desirable pharmacokinetic profile when administered to mammalian subjects. The desirable pharmacokinetic profile of the active agent compositions preferably includes, but is not limited to: (1) a $T_{max}$ for an active agent, when assayed in the plasma of a mammalian subject following administration, that is preferably less than the $T_{max}$ for a non-nanoparticulate composition of the same active agent, administered at the same dosage; (2) a $C_{max}$ for an active agent, when assayed in the plasma of a mammalian subject following administration, that is preferably greater than the $C_{max}$ for a non-nanoparticulate composition of the same active agent, administered at the same dosage; and/or (3) an AUC for an active agent, when assayed in the plasma of a mammalian subject following administration, that is preferably greater than the AUC for a non-nanoparticulate composition of the same active agent, administered at the same dosage.

The desirable pharmacokinetic profile, as used herein, is the pharmacokinetic profile measured after the initial dose of the active agent. The compositions can be formulated in any way as described herein and as known to those of skill in the art.

A preferred active agent composition of the invention, comprising at least one peptide as a surface stabilizer, exhibits in comparative pharmacokinetic testing with a non-nanoparticulate composition of the same active agent, administered at the same dosage, a $T_{max}$ not greater than about 100%, not greater than about 90%, not greater than about 80%, not greater than about 70%, not greater than about 60%, not greater than about 50%, not greater than about 40%, not greater than about 30%, not greater than about 25%, not greater than about 20%, not greater than about 15%, not greater than about 10%, or not greater than about 5% of the $T_{max}$ exhibited by the non-nanoparticulate active agent composition. This shorter $T_{max}$ translates into a faster onset of therapeutic activity.

A preferred active agent composition of the invention, comprising at least one peptide as a surface stabilizer, exhibits in comparative pharmacokinetic testing with a non-nanoparticulate composition of the same active agent, administered at the same dosage, a $C_{max}$ which is at least about 10%, at least about 20%, at least about 30%, at least about 40%, at least about 50%, at least about 60%, at least about 70%, at least about 80%, at least about 90%, at least about 100%, at least about 110%, at least about 120%, at least about 130%, at least about 140%, at least about 150%, at least about 160%, at least about 170%, at least about 180%, at least about 190%, or at least about 200% greater than the $C_{max}$ exhibited by the non-nanoparticulate active agent composition.

A preferred active agent composition of the invention, comprising at least one peptide as a surface stabilizer, exhibits in comparative pharmacokinetic testing with a non-nanoparticulate composition of the same active agent, administered at the same dosage, an AUC which is at least about 10%, at least about 20%, at least about 30%, at least about 40%, at least about 50%, at least about 60%, at least about 70%, at least about 80%, at least about 90%, at least about 100%, at least about 110%, at least about 120%, at least about 130%, at least about 140%, at least about 150%, at least about 160%, at least about 170%, at least about 180%, at least about 190%, or at least about 200% greater than the AUC exhibited by the non-nanoparticulate active agent formulation.

Any formulation giving the desired pharmacokinetic profile is suitable for administration according to the present methods.

C. The Pharmacokinetic Profiles of the Nanoparticulate Active Agent Compositions of the Invention are Preferably not Substantially Affected by the Fed or Fasted State of the Subject Ingesting the Compositions The invention encompasses nanoparticulate active agent compositions, comprising at least one peptide as a surface stabilizer, wherein preferably the pharmacokinetic profile of the active agent is not substantially affected by the fed or fasted state of a subject ingesting the composition. This means that there is no substantial difference in the quantity of active agent absorbed or the rate of active agent absorption when the nanoparticulate active agent compositions are administered in the fed versus the fasted state. Thus, the nanoparticulate active agent compositions of the invention can preferably substantially eliminate the effect of food on the pharmacokinetics of the active agent.

In another embodiment of the invention, the pharmacokinetic profile of the active agent compositions of the invention, comprising at least one peptide as a surface stabilizer, when administered to a mammal in a fasted state, is bioequivalent to the pharmacokinetic profile of the same nanoparticulate active agent composition administered at the same dosage, when administered to a mammal in a fed state.

"Bioequivalency" is preferably established by a 90% Confidence Interval (CI) of between 0.80 and 1.25 for both $C_{max}$ and AUC under U.S. Food and Drug Administration (USFDA) regulatory guidelines, or a 90% CI for AUC of between 0.80 to 1.25 and a 90% CI for $C_{max}$ of between 0.70 to 1.43 under the European Medicines Evaluation Agency (EMEA) regulatory guidelines ($T_{max}$ is not relevant for bioequivalency determinations under USFDA and EMEA regulatory guidelines).

Preferably the difference in AUC (e.g., absorption) of the nanoparticulate active agent composition of the invention, comprising at least one peptide as a surface stabilizer, when administered in the fed versus the fasted state, is less than about 100%, less than about 90%, less than about 80%, less than about 70%, less than about 60%, less than about 50%, less than about 40%, less than about 35%, less than about 30%, less than about 25%, less than about 20%, less than about 15%, less than about 10%, less than about 5%, or less than about 3%.

In addition, preferably the difference in $C_{max}$ of the nanoparticulate active agent composition of the invention, comprising at least one peptide as a surface stabilizer, when administered in the fed versus the fasted state, is less than about 100%, less than about 90%, less than about 80%, less than about 70%, less than about 60%, less than about 50%, less than about 40%, less than about 35%, less than about 30%, less than about 25%, less than about 20%, less than about 15%, less than about 10%, less than about 5%, or less than about 3%.

Finally, preferably the difference in the $T_{max}$ of the nanoparticulate active agent compositions of the invention, comprising at least one peptide as a surface stabilizer, when administered in the fed versus the fasted state, is less than about 100%, less than about 90%, less than about 80%, less than about 70%, less than about 60%, less than about 50%, less than about 40%, less than about 30%, less than about 20%, less than about 15%, less than about 10%, less than about 5%, less than about 3%, or essentially no difference.

Benefits of a dosage form that substantially eliminates the effect of food include an increase in subject convenience, thereby increasing subject compliance, as the subject does not need to ensure that they are taking a dose either with or without food.

D. Redispersibility Profiles of the Nanoparticulate Active Agent Compositions of the Invention An additional feature of the nanoparticulate active agent compositions of the invention, comprising at least one peptide as a surface stabilizer, comprising at least one peptide as a surface stabilizer, is that the compositions redisperse such that the effective average particle size of the redispersed active agent particles is less than about 2 microns. This is significant, as if upon administration the nanoparticulate active agent particles present in the compositions of the invention did not redisperse to a substantially nanoparticulate particle size, then the dosage form may lose the benefits afforded by formulating the active agent into a nanoparticulate particle size.

This is because the nanoparticulate active agent compositions of the invention benefit from the small particle size of the active agent; if the nanoparticulate active agent particles do not redisperse into the small particle sizes upon administration, then "clumps" or agglomerated active agent particles are formed. With the formation of such agglomerated particles, the bioavailability of the dosage form may fall.

Moreover, the nanoparticulate active agent compositions of the invention exhibit dramatic redispersion of the active agent particles upon administration to a mammal, such as a human or animal, as demonstrated by reconstitution in a biorelevant aqueous media. Such biorelevant aqueous media can be any aqueous media that exhibit the desired ionic strength and pH, which form the basis for the biorelevance of the media. The desired pH and ionic strength are those that are representative of physiological conditions found in the human body. Such biorelevant aqueous media can be, for example, aqueous electrolyte solutions or aqueous solutions of any salt, acid, or base, or a combination thereof, which exhibit the desired pH and ionic strength.

Biorelevant pH is well known in the art. For example, in the stomach, the pH ranges from slightly less than 2 (but typically greater than 1) up to 4 or 5. In the small intestine the pH can range from 4 to 6, and in the colon it can range from 6 to 8. Biorelevant ionic strength is also well known in the art. Fasted state gastric fluid has an ionic strength of about 0.1 M while fasted state intestinal fluid has an ionic strength of about 0.14. See e.g., Lindahl et al., "Characterization of Fluids from the Stomach and Proximal Jejunum in Men and Women," *Pharm. Res.*, 14 (4): 497-502 (1997).

It is believed that the pH and ionic strength of the test solution is more critical than the specific chemical content. Accordingly, appropriate pH and ionic strength values can be obtained through numerous combinations of strong acids, strong bases, salts, single or multiple conjugate acid-base pairs (i.e., weak acids and corresponding salts of that acid), monoprotic and polyprotic electrolytes, etc.

Representative electrolyte solutions can be, but are not limited to, HCl solutions, ranging in concentration from about 0.001 to about 0.1 M, and NaCl solutions, ranging in concentration from about 0.001 to about 0.1 M, and mixtures thereof. For example, electrolyte solutions can be, but are not limited to, about 0.1 M HCl or less, about 0.01 M HCl or less, about 0.001 M HCl or less, about 0.1 M NaCl or less, about 0.01 M NaCl or less, about 0.001 M NaCl or less, and mixtures thereof. Of these electrolyte solutions, 0.01 M HCl and/or 0.1 M NaCl, are most representative of fasted human physiological conditions, owing to the pH and ionic strength conditions of the proximal gastrointestinal tract.

Electrolyte concentrations of 0.001 M HCl, 0.01 M HCl, and 0.1 M HCl correspond to pH 3, pH 2, and pH 1, respectively. Thus, a 0.01 M HCl solution simulates typical acidic conditions found in the stomach. A solution of 0.1 M NaCl provides a reasonable approximation of the ionic strength conditions found throughout the body, including the gastrointestinal fluids, although concentrations higher than 0.1 M may be employed to simulate fed conditions within the human GI tract.

Exemplary solutions of salts, acids, bases or combinations thereof, which exhibit the desired pH and ionic strength, include but are not limited to phosphoric acid/phosphate salts+sodium, potassium and calcium salts of chloride, acetic acid/acetate salts+sodium, potassium and calcium salts of chloride, carbonic acid/bicarbonate salts+sodium, potassium and calcium salts of chloride, and citric acid/citrate salts+sodium, potassium and calcium salts of chloride.

In other embodiments of the invention, the redispersed active agent particles of the invention (redispersed in an aqueous, biorelevant, or any other suitable media) have an effective average particle size of less than about 1900 nm, less than about 1800 nm, less than about 1700 nm, less than about 1600 nm, less than about 1500 nm, less than about 1400 nm, less than about 1300 nm, less than about 1200 nm, less than about 1100 nm, less than about 1000 nm, less than about 900 nm, less than about 800 nm, less than about 700 nm, less than about 600 nm, less than about 500 nm, less than about 400 nm, less than about 300 nm, less than about 250 nm, less than about 200 nm, less than about 150 nm, less than about 100 nm, less than about 75 mm, or less than about 50 nm, as measured by light-scattering methods, microscopy, or other appropriate methods.

Redispersibility can be tested using any suitable means known in the art. See e.g., the example sections of U.S. Pat. No. 6,375,986 for "Solid Dose Nanoparticulate Compositions Comprising a Synergistic Combination of a Polymeric Surface Stabilizer and Dioctyl Sodium Sulfosuccinate."

E. Bioadhesive Nanoparticulate Active Agent Compositions

Bioadhesive nanoparticulate active agent compositions of the invention comprise at least one cationic peptide surface stabilizer, or in addition to at least one non-cationic peptide as a surface stabilizer, at least one secondary non-peptide cationic surface stabilizer. Exemplary non-peptide cationic surface stabilizers are described in more detail below. Bioadhesive formulations of active agents exhibit exceptional bioadhesion to biological surfaces, such as mucous and skin.

Cationic surface stabilizers generally confer relatively large, positive zeta potentials to particles on which they adsorb or associate. To increase the bioadhesive properties of a nanoparticulate composition, two or more cationic surface stabilizers can be utilized.

In the case of bioadhesive nanoparticulate active agent compositions, the term "bioadhesion" is used to describe the adhesion between the nanoparticulate active agent compositions and a biological substrate (i.e., gastrointestinal mucin, lung tissue, nasal mucosa, etc.). See e.g., U.S. Pat. No. 6,428, 814 for "Bioadhesive Nanoparticulate Compositions Having Cationic Surface Stabilizers," which is specifically incorporated by reference.

There are basically two mechanisms which may be responsible for this bioadhesion phenomena: mechanical or physical interactions and chemical interactions. The first of these, mechanical or physical mechanisms, involves the physical interlocking or interpenetration between a bioadhesive entity and the receptor tissue, resulting from a good wetting of the bioadhesive surface, swelling of the bioadhesive polymer, penetration of the bioadhesive entity into a crevice of the tissue surface, or interpenetration of bioadhesive composition chains with those of the mucous or other such related tissues. The second possible mechanism of bioadhesion incorporates forces such as ionic attraction, dipolar forces, van der Waals interactions, and hydrogen bonds. It is this form of bioadhesion which is primarily responsible for the bioadhesive properties of the nanoparticulate active agent compositions of the invention. However, physical and mechanical interactions may also play a secondary role in the bioadhesion of such nanoparticulate active agent compositions.

The bioadhesive active agent compositions of the invention are useful in any situation in which it is desirable to apply the compositions to a biological surface. The bioadhesive active agent compositions preferably coat the targeted surface in a continuous and uniform film that is invisible to the naked human eye.

A bioadhesive nanoparticulate active agent composition slows the transit of the composition, and some active agent particles would also most likely adhere to tissue other than the mucous cells and therefore give a prolonged exposure to the active agent, thereby increasing absorption and the bioavailability of the administered dosage.

The adhesion exhibited by the inventive compositions means that nanoparticulate active agent particles are not easily washed off, rubbed off, or otherwise removed from the biological surface for an extended period of time. The period of time in which a biological cell surface is replaced is the factor that limits retention of the bioadhesive nanoparticulate active agent particles to that biological surface.

F. Low Viscosity Active Agent Dosage Forms

A liquid dosage form of a conventional microcrystalline or non-nanoparticulate active agent composition would be expected to be a relatively large volume, highly viscous substance which would not be well accepted by patient populations. Moreover, viscous solutions can be problematic in parenteral administration because these solutions require a slow syringe push and can stick to tubing. In addition, conventional formulations of poorly water-soluble active agents tend to be unsafe for intravenous administration techniques, which are used primarily in conjunction with highly water-soluble substances.

Liquid dosage forms of the nanoparticulate active agent compositions of the invention, comprising at least one peptide as a surface stabilizer, provide significant advantages over a liquid dosage form of a conventional microcrystalline or solubilized active agent composition. The low viscosity and silky texture of liquid dosage forms of the nanoparticulate active agent compositions of the invention result in advantages in both preparation and use. These advantages include, for example: (1) better subject compliance due to the perception of a lighter formulation which is easier to consume and digest; (2) ease of dispensing because one can use a cup or a syringe; (3) potential for formulating a higher concentration of active agent resulting in a smaller dosage volume and thus less volume for the subject to consume; and (4) easier overall formulation concerns.

Liquid active agent dosage forms that are easier to consume are especially important when considering juvenile patients, terminally ill patients, and elderly patients. Viscous or gritty formulations, and those that require a relatively large dosage volume, are not well tolerated by these patient populations. Liquid oral dosage forms can be particularly preferably for patient populations who have difficulty consuming tablets, such as infants and the elderly.

The viscosities of liquid dosage forms of a nanoparticulate active agent according to the invention are preferably less than about 1/200, less than about 1/175, less than about 1/150, less than about 1/125, less than about 1/100, less than about 1/75, less than about 1/50, or less than about 1/25 of a liquid oral dosage form of a non-nanoparticulate composition of the same active agent, at about the same concentration per ml of active agent.

Typically liquid nanoparticulate active agent dosage forms of the invention, comprising at least one peptide as a surface stabilizer, have a viscosity at a shear rate of 0.1 (1/s) measured at 20° C., is from about 2000 mPa·s to about 1 mPa·s, from about 1900 mPa·s to about 1 mPa·s, from about 1800 mPa·s to about 1 mPa·s, from about 1700 mPa·s to about 1 mPa·s, from about 1600 mPa·s to about 1 mPa·s, from about 1500 mPa·s to about 1 mPa·s, from about 1400 mPa·s to about 1 mPa·s, from about 1300 mPa·s to about 1 mPa·s, from about 1200 mPa·s to about 1 mPa·s, from about 1100 mPa·s to about 1 mPa·s, from about 1000 mPa·s to about 1 mPa·s, from about 900 mPa·s to about 1 mPa·s, from about 800 mPa·s to about 1 mPa·s, from about 700 mPa·s to about 1 mPa·s, from about 600 mPa·s to about 1 mPa·s, from about 500 mPa·s to about 1 mPa·s, from about 400 mPa·s to about 1 mPa·s, from about 300 mPa·s to about 1 mPa·s, from about 200 mPa·s to about 1 mPa·s, from about 175 mPa·s to about 1 mPa·s, from about 150 mPa·s to about 1 mPa·s, from about 125 mPa·s to about 1 mPa·s, from about 100 mPa·s to about 1 mPa·s, from about 75 mPa·s to about 1 mPa·s, from about 50 mPa·s to about 1 mPa·s, from about 25 mPa·s to about 1 mPa·s, from about 15 mPa·s to about 1 mPa·s, from about 10 mPa·s to about 1 mPa·s, or from about 5 mPa·s to about 1 mPa·s. Such a viscosity is much more attractive for subject consumption and may lead to better overall subject compliance.

Viscosity is concentration and temperature dependent. Typically, a higher concentration results in a higher viscosity, while a higher temperature results in a lower viscosity. Viscosity as defined above refers to measurements taken at about 20° C. (The viscosity of water at 20° C. is 1 mPa·s.) The invention encompasses equivalent viscosities measured at different temperatures.

Another important aspect of the invention is that the nanoparticulate active agent compositions of the invention, formulated into a liquid dosage form, are not turbid. "Turbid," as used herein refers to the property of particulate matter that can be seen with the naked eye or that which can be felt as "gritty." The nanoparticulate active agent compositions of the invention, formulated into a liquid dosage form, can be poured out of or extracted from a container as easily as water, whereas a liquid dosage form of a non-nanoparticulate or solubilized composition of the same active agent is expected to exhibit notably more "sluggish" characteristics.

The liquid formulations of this invention can be formulated for dosages in any volume but preferably equivalent or smaller volumes than a liquid dosage form of a non-nanoparticulate composition of the same active agent.

G. Sterile Filtered Nanoparticulate Active Agent Compositions

The nanoparticulate active agent compositions of the invention can be sterile filtered. This obviates the need for heat sterilization, which can harm or degrade an active agent, as well as result in crystal growth and particle aggregation of the active agent.

Sterile filtration can be difficult because of the required small particle size of the composition. Filtration is an effective method for sterilizing homogeneous solutions when the membrane filter pore size is less than or equal to about 0.2 microns (200 nm) because a 0.2 micron filter is sufficient to remove essentially all bacteria. Sterile filtration is normally not used to sterilize suspensions of micron-sized active agents because the active agent particles are too large to pass through the membrane pores.

A sterile nanoparticulate active agent dosage form is particularly useful in treating immunocompromised patients, infants or juvenile patients, and the elderly, as these patient groups are the most susceptible to infection caused by a non-sterile liquid dosage form.

Because the nanoparticulate active agent compositions of the invention, comprising at least one peptide as a surface stabilizer and formulated into a liquid dosage form, can be sterile filtered, and because the compositions can have a very small active agent effective average particle size, the compositions are suitable for parenteral administration.

H. Combination Pharmacokinetic Profile Compositions

In yet another embodiment of the invention, a first nanoparticulate active agent composition providing a desired pharmacokinetic profile is co-administered, sequentially administered, or combined with at least one other active agent composition that generates a desired different pharmacokinetic profile. More than two active agent compositions can be co-administered, sequentially administered, or combined. While the first active agent composition has a nanoparticulate particle size, the additional one or more active agent compositions can be nanoparticulate, solubilized, or have a microparticulate particle size.

The second, third, fourth, etc., active agent compositions can differ from the first, and from each other, for example: (1) in the identity of the active agent; (2) in the effective average particle sizes of the active agent; or (3) in the dosage of the active agent. Such a combination composition can reduce the dose frequency required.

For example, a first active agent composition can have a nanoparticulate particle size, conferring a short $T_{max}$ and typically a higher $C_{max}$. This first active agent composition can be combined, co-administered, or sequentially administered with a second composition comprising: (1) the same active agent having a larger (but still nanoparticulate as defined herein) particle size, and therefore exhibiting slower absorption, a longer $T_{max}$, and typically a lower $C_{max}$; or (2) a microparticulate or solubilized composition of the same active agent, exhibiting a longer $T_{max}$, and typically a lower $C_{max}$.

If the second active agent composition has a nanoparticulate particle size, then preferably the active agent particles of the second composition have at least one surface stabilizer associated with the surface of the active agent particles. The one or more surface stabilizers can be the same as or different from the surface stabilizer(s) present in the first active agent composition.

Preferably where co-administration of a "fast-acting" formulation and a "longer-lasting" formulation is desired, the two formulations are combined within a single composition, for example a dual-release composition.

I. Miscellaneous Benefits of the Nanoparticulate Active Agent Compositions of the Invention The nanoparticulate active agent compositions of the invention, comprising at least one peptide as a surface stabilizer, preferably exhibit an increased rate of dissolution as compared to microcrystalline or non-nanoparticulate forms of the same active agent. In addition, the nanoparticulate active agent compositions preferably exhibit improved performance characteristics for oral, intravenous, subcutaneous, or intramuscular injection, such as higher dose loading and smaller tablet or liquid dose volumes. Moreover, the nanoparticulate active agent compositions of the invention do not require organic solvents or pH extremes.

II. Compositions

The compositions of the invention comprise a nanoparticulate active agent and at least one peptide as a surface stabilizer adsorbed to or associated with the surface of the active agent. In addition, the compositions can comprise one or more secondary surface stabilizers. Surface stabilizers useful herein physically adhere to or associate with the surface of the nanoparticulate active agent but do not chemically react with the active agent or itself. Individual molecules of the surface stabilizer are essentially free of intermolecular cross-linkages.

The present invention also includes nanoparticulate active agent compositions, having at least one peptide as a surface stabilizer, formulated into compositions together with one or more non-toxic physiologically acceptable carriers, adjuvants, or vehicles, collectively referred to as carriers.

A. Peptide Surface Stabilizer

The choice of a surface stabilizer is non-trivial and usually requires extensive experimentation to realize a desirable formulation. Accordingly, the present invention is directed to the surprising discovery that a peptide, used as a nanoparticulate surface stabilizer, yields stable nanoparticulate active agent compositions that exhibit low degrees of aggregation.

A "peptide" is defined as any compound consisting of two or more amino acids, which are the basic structural units or "building blocks" of peptides. All peptides in all species, from bacteria to humans, are constructed from the same set of twenty commonly occurring, genetically encoded amino acids, as shown in the table below.

Each amino acid contains an "amine" group ($NH_3$), a "carboxy" group (COOH), a hydrogen atom, and a distinctive R group, or sidechain, bonded to a carbon atom. The amino acids vary in their sidechains, with variations in size, shape, charge, hydrogen-bonding capacity, and chemical reactivity. See e.g., L. Stryer, *Biochemistry*, $3^{rd}$ Edition, 1-40 (W.H. Freeman & Co., NY, 1988).

| Amino Acid | 3 Letter Abbreviation | 1 Letter Abbreviation |
| --- | --- | --- |
| alanine | ALA | A |
| asparagine | ASN | N |
| aspartic acid | ASP | D |
| arginine | ARG | R |
| cysteine | CYS | C |
| glutamic acid | GLU | E |
| glutamine | GLN | Q |
| glycine | GLY | G |
| histidine | HIS | H |
| isoleucine | ILE | I |
| leucine | LEU | L |
| lysine | LYS | K |
| methionine | MET | M |
| phenylalanine | PHE | F |
| proline | PRO | P |
| serine | SER | S |
| threonine | THR | T |
| tryptophan | TRP | W |
| tyrosine | TYR | Y |
| valine | VAL | V |
| aspartic acid or asparagines | ASX | |
| glutamic acid or glutamine | GLX | |
| Unknown or other | Xaa | X |

Peptides useful in the present invention can also comprise substituents other than amino acids. There are also naturally occurring chemical modifications of these twenty genetically encoded amino acids, such as hydroxylation of proline, addition of carbohydrates and lipids, and phosphorylation of serine and tyrosine. In addition, D-isomers of the amino acids, as opposed to the L-isomers found in naturally-occurring peptides and proteins, have been synthesized.

The amino acids of a peptide are connected by a amide, covalent linkage between the alpha carboxyl group of one amino acid and the alpha amino group of another amino acid. Many amino acids are joined by peptide bonds to form a polypeptide chain, which is unbranched. A polypeptide chain is a long peptide chain, consisting of a regularly repeating part, called the main chain, and a variable part, comprising the distinctive sidechains. Disulfide cross-links can be formed by cysteine residues in polypeptides. Most natural polypeptide chains contain between 50 and 2000 amino acids residues. The mean molecular weight of an amino acid residue is about 110 daltons, and so the molecular weights of most polypeptide chains are between 5500 and 220,000. See e.g. L. Stryer, *Biochemistry*, $3^{rd}$ Edition, p. 22 (W.H. Freeman & Co., NY, 1988).

A protein is a large macromolecule composed of one or more polypeptide chains. In the context of the present invention, a "peptide" refers to a peptide or a polypeptide, but not a protein.

Preferably, the peptide surface stabilizers of the invention are water soluble. By "water soluble," it is meant that the peptide has a water solubility of greater than about 1 mg/mL, greater than about 10 mg/mL, greater than about 20 mg/mL, or greater than about 30 mg/mL. This is in contrast to prior art compositions teaching the use of a peptide as an active agent in a nanoparticulate active agent composition. See e.g., U.S. Pat. Nos. 6,270,806; 6,592,903; 6,428,814; and 6,375,986. In such prior art references, when a peptide is utilized as an active agent in a nanoparticulate composition, the peptide is poorly water soluble.

There is an extensive catalog of commercially available peptides that can be used in the compositions of the invention. For example, the on-line peptide catalog http://www.peptide-catalog.com/PC/Peptides provides a list of hundreds of commercially available peptides, along with their structure and molecular weight. In addition, to the many commercially available peptides, custom peptides can be made and utilized in the compositions of the invention.

A preferred peptide surface stabilizer is poly(Lysine, Tryptophan)) 4:1 hydrobromide.

B. Secondary or Auxiliary Surface Stabilizers

The compositions of the invention can also include one or more auxiliary non-peptide surface stabilizers in addition to the at least one peptide surface stabilizer.

The auxiliary surface stabilizers of the invention are preferably adsorbed on, or associated with, the surface of the active agent particles. The auxiliary surface stabilizers especially useful herein preferably do not chemically react with the active agent particles or itself. Preferably, individual molecules of the auxiliary surface stabilizer are essentially free of intermolecular cross-linkages.

Two or more auxiliary surface stabilizers can be employed in the compositions and methods of the invention.

Suitable surface stabilizers can preferably be selected from known organic and inorganic pharmaceutical excipients. Such excipients include various polymers, low molecular weight oligomers, natural products, and surfactants. Preferred auxiliary surface stabilizers include nonionic, anionic, cationic, zwitterionic, and ionic surfactants.

Representative examples of secondary surface stabilizers include gelatin, casein, lecithin (phosphatides), dextran, gum acacia, cholesterol, tragacanth, stearic acid, benzalkonium chloride, calcium stearate, glycerol monostearate, cetostearyl alcohol, cetomacrogol emulsifying wax, sorbitan esters, polyoxyethylene alkyl ethers (e.g., macrogol ethers such as cetomacrogol 1000), polyoxyethylene castor oil derivatives, polyoxyethylene sorbitan fatty acid esters (e.g., the commercially available Tweens® such as e.g., Tween 20® and Tween 80® (ICI Speciality Chemicals)); polyethylene glycols (e.g., Carbowaxs 3550® and 934® (Union Carbide)), polyoxyethylene stearates, colloidal silicon dioxide, phosphates, sodium dodecylsulfate, carboxymethylcellulose calcium, carboxymethylcellulose sodium, methylcellulose, hydroxyethylcellulose, hydroxypropyl celluloses (e.g., HPC, HPC-SL, and HPC-L), hydroxypropyl methylcellulose (HPMC), hydroxypropylmethyl-cellulose phthalate, noncrystalline cellulose, magnesium aluminum silicate, triethanolamine, polyvinyl alcohol (PVA), polyvinylpyrrolidone (PVP), 4-(1,1,3,3-tetramethylbutyl)-phenol polymer with ethylene oxide and formaldehyde (also known as tyloxapol, superione, and triton), poloxamers (e.g., Pluronics F68® and F108®, which are block copolymers of ethylene oxide and propylene oxide); poloxamines (e.g., Tetronic 908®, also known as Poloxamine 908®, which is a tetrafunctional block copolymer derived from sequential addition of propylene oxide and ethylene oxide to ethylenediamine (BASF Wyandotte Corporation, Parsippany, N.J.)); Tetronic 1508® (T-1508) (BASF Wyandotte Corporation), dialkylesters of sodium sulfosuccinic acid (e.g., Aerosol OT®, which is a dioctyl ester of sodium sulfosuccinic acid (DOSS) (American Cyanamid)); Duponol P®, which is a sodium lauryl sulfate (DuPont); Tritons X-200®, which is an alkyl aryl polyether sulfonate (Rohm and Haas); Crodestas F-110®, which is a mixture of sucrose stearate and sucrose distearate (Croda Inc.); p-isononylphenoxypoly-(glycidol), also known as Olin-10G® or Surfactant 10-G® (Olin Chemicals, Stamford, Conn.); Crodestas SL-40® (Croda, Inc.); and SA9OHCO, which is $C_{18}H_{37}CH_2C(O)N(CH_3)$—$CH_2(CHOH)_4$ $(CH_2OH)_2$ (Eastman Kodak Co.); decanoyl-N-methylglucamide; n-decyl β-D-glucopyranoside; n-decyl β-D-maltopyranoside; n-dodecyl β-D-glucopyranoside; n-dodecyl β-D-maltoside; heptanoyl-N-methylglucamide; n-heptyl-β-D-glucopyranoside; n-heptyl β-D-thioglucoside; n-hexyl β-D-glucopyranoside; nonanoyl-N-methylglucamide; n-noyl β-D-glucopyranoside; octanoyl-N-methylglucamide; n-octyl-β-D-glucopyranoside; octyl β-D-thioglucopyranoside; lysozyme, PEG-derivatized phospholipid, PEG-derivatized cholesterol, PEG-derivatized cholesterol derivative, PEG-derivatized vitamin A, PEG-derivatized vitamin E, random copolymers of vinyl pyrrolidone and vinyl acetate, and the like.

Examples of useful cationic surface stabilizers include but are not limited to, polymers, biopolymers, polysaccharides, cellulosics, alginates, phospholipids, and nonpolymeric compounds, such as zwitterionic stabilizers, poly-n-methylpyridinium, anthryul pyridinium chloride, cationic phospholipids, a charged phospholipid such as dimyristoyl phophatidyl glycerol, chitosan, polylysine, polyvinylimidazole, polybrene, polymethylmethacrylate trimethylammoniumbromide bromide (PMMTMABr), hexyldesyltrimethylammonium bromide (HDMAB), and polyvinylpyrrolidone-2-dimethylaminoethyl methacrylate dimethyl sulfate.

Other useful cationic stabilizers include, but are not limited to, cationic lipids, sulfonium, phosphonium, and quarternary ammonium compounds, such as stearyltrimethylammonium chloride, benzyl-di(2-chloroethyl)ethylammonium bromide, coconut trimethyl ammonium chloride or bromide, coconut methyl dihydroxyethyl ammonium chloride or bromide, dodecyl trimethyl ammonium bromide, decyl triethyl ammonium chloride, decyl dimethyl hydroxyethyl ammonium chloride or bromide, $C_{12-15}$dimethyl hydroxyethyl ammonium chloride or bromide, coconut dimethyl hydroxyethyl ammonium chloride or bromide, myristyl trimethyl ammonium methyl sulphate, lauryl dimethyl benzyl ammonium chloride or bromide, lauryl dimethyl (ethenoxy)$_4$ ammonium chloride or bromide, N-alkyl ($C_{12-18}$)dimethylbenzyl ammonium chloride, N-alkyl ($C_{14-18}$)dimethyl-benzyl ammonium chloride, N-tetradecylidmethylbenzyl ammonium chloride monohydrate, dimethyl didecyl ammonium chloride, N-alkyl and ($C_{12-14}$) dimethyl 1-napthylmethyl ammonium chloride, trimethylammonium halide, alkyl-trimethylammonium salts and dialkyl-dimethylammonium salts, lauryl trimethyl ammonium chloride, ethoxylated alkyamidoalkyldialkylammonium salt and/or an ethoxylated trialkyl ammonium salt, dialkylbenzene dialkylammonium chloride, N-didecyldimethyl ammonium chloride, N-tetradecyldimethylbenzyl ammonium, chloride monohydrate, N-alkyl($C_{12-14}$) dimethyl 1-naphthylmethyl ammonium chloride and dodecyldimethylbenzyl ammonium chloride, dialkyl benzenealkyl ammonium chloride, lauryl trimethyl ammonium chloride, alkylbenzyl methyl ammonium chloride, alkyl benzyl dimethyl ammonium bromide, $C_{12}$, $C_{15}$, $C_{17}$ trimethyl ammonium bromides, dodecylbenzyl triethyl ammonium chloride, poly-diallyldimethylammonium chloride (DADMAC), dimethyl ammonium chlorides, alkyldimethylammonium halogenides, tricetyl methyl ammonium chloride, decyltrimethylammonium bromide, dodecyltriethylammonium bromide, tetradecyltrimethylammonium bromide, methyl trioctylammonium chloride (ALIQUAT 336™), POLYQUAT 10™, tetrabutylammonium bromide, benzyl trimethylammonium bromide, choline esters (such as choline esters of fatty acids), benzalkonium chloride, stearalkonium chloride compounds (such as stearyltrimonium chloride and Di-stearyldimonium chloride), cetyl pyridinium bromide or chloride, halide salts of quaternized polyoxyethylalkylamines, MIRAPOL™ and ALKAQUAT™ (Alkaril Chemical Company), alkyl pyridinium salts; amines, such as alkylamines, dialkylamines, alkanolamines, polyethylenepolyamines, N,N-dialkylaminoalkyl acrylates, and vinyl pyridine, amine salts, such as lauryl amine acetate, stearyl amine acetate, alkylpyridinium salt, and alkylimidazolium salt, and amine oxides; imide azolinium salts; protonated quaternary acrylamides; methylated quaternary polymers, such as poly[diallyl dimethylammonium chloride] and poly-[N-methyl vinyl pyridinium chloride]; and cationic guar.

Such exemplary cationic surface stabilizers and other useful cationic surface stabilizers are described in J. Cross and E. Singer, *Cationic Surfactants: Analytical and Biological Evaluation* (Marcel Dekker, 1994); P. and D. Rubingh (Editor), *Cationic Surfactants: Physical Chemistry* (Marcel Dekker, 1991); and J. Richmond, *Cationic Surfactants: Organic Chemistry*, (Marcel Dekker, 1990).

Particularly preferred nonpolymeric primary stabilizers are any nonpolymeric compound, such benzalkonium chloride, a carbonium compound, a phosphonium compound, an oxonium compound, a halonium compound, a cationic organometallic compound, a quarternary phosphorous compound, a pyridinium compound, an anilinium compound, an immonium compound, a hydroxylammonium compound, a primary ammonium compound, a secondary ammonium compound, a tertiary ammonium compound, and quarternary ammonium compounds of the formula $NR_1R_2R_3R_4^{(+)}$. For compounds of the formula $NR_1R_2R_3R_4^{(+)}$:

(i) none of $R_1$-$R_4$ are $CH_3$;
(ii) one of $R_1$-$R_4$ is $CH_3$;
(iii) three of $R_1$-$R_4$ are $CH_3$;

(iv) all of $R_1$-$R_4$ are $CH_3$;
(v) two of $R_1$-$R_4$ are $CH_3$, one of $R_1$-$R_4$ is $C_6H_5CH_2$, and one of $R_1$-$R_4$ is an alkyl chain of seven carbon atoms or less;
(vi) two of $R_1$-$R_4$ are $CH_3$, one of $R_1$-$R_4$ is $C_6H_5CH_2$, and one of $R_1$-$R_4$ is an alkyl chain of nineteen carbon atoms or more;
(vii) two of $R_1$-$R_4$ are $CH_3$ and one of $R_1$-$R_4$ is the group $C_6H_5(CH_2)_n$, where n>1;
(viii) two of $R_1$-$R_4$ are $CH_3$, one of $R_1$-$R_4$ is $C_6H_5CH_2$, and one of $R_1$-$R_4$ comprises at least one heteroatom;
(ix) two of $R_1$-$R_4$ are $CH_3$, one of $R_1$-$R_4$ is $C_6H_5CH_2$, and one of $R_1$-$R_4$ comprises at least one halogen;
(x) two of $R_1$-$R_4$ are $CH_3$, one of $R_1$-$R_4$ is $C_6H_5CH_2$, and one of $R_1$-$R_4$ comprises at least one cyclic fragment;
(xi) two of $R_1$-$R_4$ are $CH_3$ and one of $R_1$-$R_4$ is a phenyl ring; or
(xii) two of $R_1$-$R_4$ are $CH_3$ and two of $R_1$-$R_4$ are purely aliphatic fragments.

Such compounds include, but are not limited to, behenalkonium chloride, benzethonium chloride, cetylpyridinium chloride, behentrimonium chloride, lauralkonium chloride, cetalkonium chloride, cetrimonium bromide, cetrimonium chloride, cethylamine hydrofluoride, chlorallylmethenamine chloride (Quaternium-15), distearyldimonium chloride (Quaternium-5), dodecyl dimethyl ethylbenzyl ammonium chloride(Quaternium-14), Quaternium-22, Quaternium-26, Quaternium-18 hectorite, dimethylaminoethylchloride hydrochloride, cysteine hydrochloride, diethanolammonium POE (10) oletyl ether phosphate, diethanolammonium POE (3)oleyl ether phosphate, tallow alkonium chloride, dimethyl dioctadecylammoniumbentonite, stearalkonium chloride, domiphen bromide, denatonium benzoate, myristalkonium chloride, laurtrimonium chloride, ethylenediamine dihydrochloride, guanidine hydrochloride, pyridoxine HCl, iofetamine hydrochloride, meglumine hydrochloride, methylbenzethonium chloride, myrtrimonium bromide, oleyltrimonium chloride, polyquaternium-1, procainehydrochloride, cocobetaine, stearalkonium bentonite, stearalkoniumhectonite, stearyl trihydroxyethyl propylenediamine dihydrofluoride, tallowtrimonium chloride, and hexadecyltrimethyl ammonium bromide.

Most of these surface stabilizers are known pharmaceutical excipients and are described in detail in the *Handbook of Pharmaceutical Excipients*, published jointly by the American Pharmaceutical Association and The Pharmaceutical Society of Great Britain (The Pharmaceutical Press, 1986), specifically incorporated by reference. The surface stabilizers are commercially available and/or can be prepared by techniques known in the art.

C. Active Agents

The nanoparticles of the invention comprise at least one active, therapeutic, or diagnostic agent, collectively referred to as a "drug." A therapeutic agent can be a pharmaceutical agent, including biologics such as proteins, peptides, and nucleotides, or a diagnostic agent, such as a contrast agent, including x-ray contrast agents.

The active agent exists as a crystalline phase, an amorphous phase, a semi-amorphous phase, a semi-crystalline phase, or mixtures thereof. The crystalline phase differs from a non-crystalline or amorphous phase which results from precipitation techniques, such as those described in EP Patent No. 275,796.

The invention can be practiced with a wide variety of active agents. The active agent is preferably present in an essentially pure form, is poorly soluble, and is dispersible in at least one liquid dispersion media. By "poorly soluble" it is meant that the active agent has a solubility in a liquid dispersion media of less than about 30 mg/mL, less than about 20 mg/mL, less than about 10 mg/mL, or less than about 1 mg/mL. Useful liquid dispersion medias include, but are not limited to, water, aqueous salt solutions, safflower oil, and solvents such as ethanol, t-butanol, hexane, and glycol. A preferred liquid dispersion media is water.

Two or more active agents can be used in combination.

1. Active Agents Generally

The active agent can be selected from a variety of known classes of drugs, including, for example, nutraceuticals, COX-2 inhibitors, retinoids, anticancer agents, NSAIDS, proteins, peptides, nucleotides, anti-obesity drugs, nutraceuticals, dietary supplements, carotenoids, corticosteroids, elastase inhibitors, anti-fungals, oncology therapies, antiemetics, analgesics, cardiovascular agents, anti-inflammatory agents, anthelmintics, anti-arrhythmic agents, antibiotics (including penicillins), anticoagulants, antidepressants, antidiabetic agents, antiepileptics, antihistamines, antihypertensive agents, antimuscarinic agents, antimycobacterial agents, antineoplastic agents, immunosuppressants, antithyroid agents, antiviral agents, anxiolytics, sedatives (hypnotics and neuroleptics), astringents, beta-adrenoceptor blocking agents, blood products and substitutes, cardiac inotropic agents, contrast media, corticosteroids, cough suppressants (expectorants and mucolytics), diagnostic agents, diagnostic imaging agents, diuretics, dopaminergics (antiparkinsonian agents), haemostatics, immunological agents, lipid regulating agents, muscle relaxants, parasympathomimetics, parathyroid calcitonin and biphosphonates, prostaglandins, radio-pharmaceuticals, sex hormones (including steroids), anti-allergic agents, stimulants and anoretics, sympathomimetics, thyroid agents, vasodilators, and xanthines.

Examples of representative active agents useful in this invention include, but are not limited to, acyclovir, alprazolam, altretamine, amiloride, amiodarone, benztropine mesylate, bupropion, cabergoline, candesartan, cerivastatin, chlorpromazine, ciprofloxacin, cisapride, clarithromycin, clonidine, clopidogrel, cyclobenzaprine, cyproheptadine, delavirdine, desmopressin, diltiazem, dipyridamole, dolasetron, enalapril maleate, enalaprilat, famotidine, felodipine, furazolidone, glipizide, irbesartan, ketoconazole, lansoprazole, loratadine, loxapine, mebendazole, mercaptopurine, milrinone lactate, minocycline, mitoxantrone, nelfinavir mesylate, nimodipine, norfloxacin, olanzapine, omeprazole, penciclovir, pimozide, tacolimus, quazepam, raloxifene, rifabutin, rifampin, risperidone, rizatriptan, saquinavir, sertraline, sildenafil, acetyl-sulfisoxazole, temazepam, thiabendazole, thioguanine, trandolapril, triamterene, trimetrexate, troglitazone, trovafloxacin, verapamil, vinblastine sulfate, mycophenolate, atovaquone, atovaquone, proguanil, ceftazidime, cefuroxime, etoposide, terbinafine, thalidomide, fluconazole, amsacrine, dacarbazine, teniposide, and acetylsalicylate.

Exemplary nutraceuticals and dietary supplements are disclosed, for example, in Roberts et al., *Nutraceuticals: The Complete Encyclopedia of Supplements, Herbs, Vitamins, and Healing Foods* (American Nutraceutical Association, 2001), which is specifically incorporated by reference. A nutraceutical or dietary supplement, also known as a phytochemical or functional food, is generally any one of a class of dietary supplements, vitamins, minerals, herbs, or healing foods that have medical or pharmaceutical effects on the body. Exemplary nutraceuticals or dietary supplements include, but are not limited to, lutein, folic acid, fatty acids (e.g., DHA and ARA), fruit and vegetable extracts, vitamin and mineral supplements, phosphatidylserine, lipoic acid, melatonin, glucosamine/chondroitin, Aloe Vera, Guggul, glutamine, amino acids (e.g., iso-leucine, leucine, lysine, methionine, phenylanine, threonine, tryptophan, and valine), green tea, lycopene, whole foods, food additives, herbs, phytonutrients, antioxidants, flavonoid constituents of fruits, evening primrose oil, flax seeds, fish and marine animal oils, and probiotics. Nutraceuticals and dietary supplements also include bio-engineered foods genetically engineered to have a desired property, also known as "pharmafoods."

Active agents to be administered in an aerosol formulation are preferably selected from the group consisting of proteins, peptide, bronchodilators, corticosteroids, elastase inhibitors, analgesics, anti-fungals, cystic-fibrosis therapies, asthma therapies, emphysema therapies, respiratory distress syndrome therapies, chronic bronchitis therapies, chronic obstructive pulmonary disease therapies, organ-transplant rejection therapies, therapies for tuberculosis and other infections of the lung, fungal infection therapies, respiratory illness therapies associated with acquired immune deficiency syndrome, an oncology drug, an anti-emetic, an analgesic, and a cardiovascular agent.

2. Anticancer Active Agents

Useful anticancer agents are preferably selected from alkylating agents, antimetabolites, natural products, hormones and antagonists, and miscellaneous agents, such as radiosensitizers.

Examples of alkylating agents include: (1) alkylating agents having the bis-(2-chloroethyl)-amine group such as, for example, chlormethine, chlorambucile, melphalan, uramustine, mannomustine, extramustinephoshate, mechlorethaminoxide, cyclophosphamide, ifosfamide, and trifosfamide; (2) alkylating agents having a substituted aziridine group such as, for example, tretamine, thiotepa, triaziquone, and mitomycine; (3) alkylating agents of the alkyl sulfonate type, such as, for example, busulfan, piposulfan, and piposulfam; (4) alkylating N-alkyl-N-nitrosourea derivatives, such as, for example, carmustine, lomustine, semustine, or streptozotocine; and (5) alkylating agents of the mitobronitole, dacarbazine and procarbazine type.

Examples of antimetabolites include: (1) folic acid analogs, such as, for example, methotrexate; (2) pyrimidine analogs such as, for example, fluorouracil, floxuridine, tegafur, cytarabine, idoxuridine, and flucytosine; and (3) purine derivatives such as, for example, mercaptopurine, thioguanine, azathioprine, tiamiprine, vidarabine, pentostatin, and puromycine.

Examples of natural products include: (1) vinca alkaloids, such as, for example, vinblastine and vincristine; (2) epipodophylotoxins, such as, for example, etoposide and teniposide; (3) antibiotics, such as, for example, adriamycine, daunomycine, doctinomycin, daunorubicin, doxorubicin, mithramycin, bleomycin, and mitomycin; (4) enzymes, such as, for example, L-asparaginase; (5) biological response modifiers, such as, for example, alpha-interferon; (6) camptothecin; (7) taxol; and (8) retinoids, such as retinoic acid.

Examples of hormones and antagonists include: (1) adrenocorticosteroids, such as, for example, prednisone; (2) progestins, such as, for example, hydroxyprogesterone caproate, medroxyprogesterone acetate, and megestrol acetate; (3) estrogens, such as, for example, diethylstilbestrol and ethinyl estradiol; (4) antiestrogens, such as, for example, tamoxifen; (5) androgens, such as, for example, testosterone propionate and fluoxymesterone; (6) antiandrogens, such as, for example, flutamide; and (7) gonadotropin-releasing hormone analogs, such as, for example, leuprolide.

Examples of miscellaneous agents include: (1) radiosensitizers, such as, for example, 1,2,4-benzotriazin-3-amine 1,4-dioxide (SR 4889) and 1,2,4-benzotriazine-7-amine 1,4-dioxide (WIN 59075); (2) platinum coordination complexes such as cisplatin and carboplatin; (3) anthracenediones, such as, for example, mitoxantrone; (4) substituted ureas, such as, for example, hydroxyurea; and (5) adrenocortical suppressants, such as, for example, mitotane and aminoglutethimide.

In addition, the anticancer agent can be an immunosuppressive drug, such as, for example, cyclosporine, azathioprine, sulfasalazine, methoxsalen, and thalidomide.

The anticancer agent can also be a COX-2 inhibitor.

3. Analgesic Active Agents

An analgesic can be, for example, an NSAID or a COX-2 inhibitor.

Exemplary NSAIDS that can be formulated in compositions of the invention include, but are not limited to, suitable nonacidic and acidic compounds. Suitable nonacidic compounds include, for example, nabumetone, tiaramide, proquazone, bufexamac, flumizole, epirazole, tinoridine, timegadine, and dapsone. Suitable acidic compounds include, for example, carboxylic acids and enolic acids. Suitable carboxylic acid NSAIDs include, for example: (1) salicylic acids and esters thereof, such as aspirin, diflunisal, benorylate, and fosfosal; (2) acetic acids, such as phenylacetic acids, including diclofenac, alclofenac, and fenclofenac; (3) carbo- and heterocyclic acetic acids such as etodolac, indomethacin, sulindac, tolmetin, fentiazac, and tilomisole; (4) propionic acids, such as carprofen, fenbufen, flurbiprofen, ketoprofen, oxaprozin, suprofen, tiaprofenic acid, ibuprofen, naproxen, fenoprofen, indoprofen, and pirprofen; and (5) fenamic acids, such as flufenamic, mefenamic, meclofenamic, and niflumic. Suitable enolic acid NSAIDs include, for example: (1) pyrazolones such as oxyphenbutazone, phenylbutazone, apazone, and feprazone; and (2) oxicams such as piroxicam, sudoxicam, isoxicam, and tenoxicam.

Exemplary COX-2 inhibitors that can be formulated in combination with the nanoparticulate nimesulide composition of the invention include, but are not limited to, celecoxib (SC-58635, CELEBREX®, Pharmacia/Searle & Co.), rofecoxib (MK-966, L-748731, VIOXX®, Merck & Co.), meloxicam (MOBIC®, co-marketed by Abbott Laboratories, Chicago, Ill., and Boehringer Ingelheim Pharmaceuticals), valdecoxib (BEXTRA®, G.D. Searle & Co.), parecoxib (G.D. Searle & Co.), etoricoxib (MK-663; Merck), SC-236 (chemical name of 4-[5-(4-chlorophenyl)-3-(trifluoromethyl)-1H-pyrazol-1-yl)]benzenesulfonamide; G.D. Searle & Co., Skokie, Ill.); NS-398 (N-(2-cyclohexyloxy-4-nitrophenyl)methane sulfonamide; Taisho Pharmaceutical Co., Ltd., Japan); SC-58125 (methyl sulfone spiro(2.4)hept-5-ene I; Pharmacia/Searle & Co.); SC-57666 (Pharmacia/Searle & Co.); SC-558 (Pharmacia/Searle & Co.); SC-560 (Pharmacia/Searle & Co.); etodolac (Lodine®, Wyeth-Ayerst Laboratories, Inc.); DFU (5,5-dimethyl-3-(3-fluorophenyl)-4-(4-methylsulfonyl)phenyl 2(5H)-furanone); monteleukast (MK-476), L-745337 ((5-methanesulphonamide-6-(2,4-difluorothio-phenyl)-1-indanone), L-761066, L-761000, L-748780 (all Merck & Co.); DUP-697 (5-Bromo-2-(4-fluorophenyl)-3-(4-(methylsulfonyl)phenyl; DuPont Merck Pharmaceutical Co.); PGV 20229 (1-(7-tert.-butyl-2,3-dihydro-3,3-dimethylbenzo(b)furan-5-yl)-4-cyclopropylbutan-1-one; Procter & Gamble Pharmaceuticals); iguratimod (T-614; 3-formylamino-7-methylsulfonylamino-6-phenoxy-4H-1-benzopyran-4-one; Toyama Corp., Japan); BF 389 (Biofor, USA); CL 1004 (PD 136095), PD 136005, PD 142893, PD 138387, and PD 145065 (all Parke-Davis/Warner-Lambert Co.); flurbiprofen (ANSAID®; Pharmacia & Upjohn); nabumetone (FELAFEN®; SmithKline Beecham, plc); flosulide (CGP 28238; Novartis/Ciba Geigy);

piroxicam (FELDANE®; Pfizer); diclofenac (VOLTAREN® and CATAFLAM®, Novartis); lumiracoxib (COX-189; Novartis); D 1367 (Celltech Chiroscience, plc); R 807 (3 benzoyldifluoromethane sulfonanilide, diflumidone); JTE-522 (Japan Tobacco, Japan); FK-3311 (4'-Acetyl-2'-(2, 4-difluorophenoxy)methanesulfonanilide), FK 867, FR 140423, and FR 115068 (all Fujisawa, Japan); GR 253035 (Glaxo Wellcome); RWJ 63556 (Johnson & Johnson); RWJ 20485 (Johnson & Johnson); ZK 38997 (Schering); S 2474 ((E)-(5)-(3,5-di-tert-butyl-4-hydroxybenzylidene)-2-ethyl-1,2-isothiazolidine-1,1-dioxide indomethacin; Shionogi & Co., Ltd., Japan); zomepirac analogs, such as RS 57067 and RS 104897 (Hoffmann La Roche); RS 104894 (Hoffmann La Roche); SC 41930 (Monsanto); pranlukast (SB 205312, Ono-1078, ONON®, ULTAIR®; SmithKline Beecham); SB 209670 (SmithKline Beecham); and APHS (heptinylsulfide).

D. Nanoparticulate Active Agent Particle Size

The compositions of the invention contain nanoparticulate active agent particles which have an effective average particle size of less than about 2000 nm (i.e., 2 microns). In other embodiments of the invention, the active agent particles have a size of less than about 1900 nm, less than about 1800 nm, less than about 1700 nm, less than about 1600 nm, less than about 1500 nm, less than about 1400 nm, less than about 1300 nm, less than about 1200 nm, less than about 1100 nm, less than about 1000 nm, less than about 900 nm, less than about 800 nm, less than about 700 nm, less than about 600 nm, less than about 500 nm, less than about 400 nm, less than about 300 nm, less than about 250 nm, less than about 200 nm, less than about 150 nm, less than about 100 nm, less than about 75 nm, or less than about 50 nm, as measured by light-scattering methods, microscopy, or other appropriate methods.

By "an effective average particle size of less than about 2000 nm" it is meant that at least 50% by weight of the active agent particles have a particle size less than the effective average, i.e., less than about 2000 nm, 1900 m, 1800 nm, etc., when measured by the above-noted techniques. In other embodiments of the invention, at least about 70%, at least about 90%, at least about 95%, or at least about 99% of the active agent particles have a particle size less than the effective average, i.e., less than about 2000 nm, 1900 nm, 1800 nm, etc.

If the nanoparticulate active agent composition is combined with a conventional active agent composition, then such a composition is either solubilized or has an effective average particle size greater than about 2 microns. By "an effective average particle size of greater than about 2 microns" it is meant that at least 50% of the microparticulate active agent particles have a particle size greater than about 2 microns, by weight, when measured by the above-noted techniques. In other embodiments of the invention, at least about 70%, at least about 90%, at least about 95%, or at least about 99%, by weight, of the microparticulate active agent particles have a particle size greater than about 2 microns.

In the present invention, the value for D50 of a nanoparticulate active agent composition is the particle size below which 50% of the active agent particles fall, by weight. Similarly, D90 and D99 are the particle sizes below which 90% and 99%, respectively, of the active agent particles fall, by weight.

5. Concentration of Nanoparticulate Active Agent and Peptide Stabilizer

The relative amounts of active agent and peptide surface stabilizer, and optionally one or more secondary surface stabilizers, can vary widely. The optimal amount of the individual components can depend, for example, upon the particular active agent selected, the hydrophilic lipophilic balance (HLB), melting point, and the surface tension of water solutions of the stabilizer, etc.

The concentration of the peptide surface stabilizer can vary from about 0.5% to about 99.999%, from about 5.0% to about 99.9%, or from about 10% to about 99.5%, by weight, based on the total combined dry weight of the at least one active agent and at least one peptide surface stabilizer, not including other excipients.

The concentration of the at least one active agent can vary from about 99.5% to about 0.001%, from about 95% to about 0.1%, or from about 90% to about 0.5%, by weight, based on the total combined dry weight of the active agent and at least one peptide surface stabilizer, not including other excipients.

B. Methods of Making Nanoparticulate Active Agent Formulations

The nanoparticulate active agent compositions of the invention, comprising at least one peptide as a surface stabilizer, can be made using, for example, milling, homogenization, or precipitation techniques. Exemplary methods of making nanoparticulate compositions are described in the '684 patent. Methods of making nanoparticulate active agent compositions are also described in U.S. Pat. No. 5,518,187 for "Method of Grinding Pharmaceutical Substances;" U.S. Pat. No. 5,718,388 for "Continuous Method of Grinding Pharmaceutical Substances;" U.S. Pat. No. 5,862,999 for "Method of Grinding Pharmaceutical Substances;" U.S. Pat. No. 5,665,331 for "Co-Microprecipitation of Nanoparticulate Pharmaceutical Agents with Crystal Growth Modifiers;" U.S. Pat. No. 5,662,883 for "Co-Microprecipitation of Nanoparticulate Pharmaceutical Agents with Crystal Growth Modifiers;" U.S. Pat. No. 5,560,932 for "Microprecipitation of Nanoparticulate Pharmaceutical Agents;" U.S. Pat. No. 5,543,133 for "Process of Preparing X-Ray Contrast Compositions Containing Nanoparticles;" U.S. Pat. No. 5,534,270 for "Method of Preparing Stable Drug Nanoparticles;" U.S. Pat. No. 5,510,118 for "Process of Preparing Therapeutic Compositions Containing Nanoparticles;" and U.S. Pat. No. 5,470,583 for "Method of Preparing Nanoparticle Compositions Containing Charged Phospholipids to Reduce Aggregation," all of which are specifically incorporated by reference.

The resultant nanoparticulate active agent compositions can be utilized in any desired dosage form.

1. Milling to Obtain Nanoparticulate Active Agent Dispersions

Milling the active agent to obtain a nanoparticulate dispersion comprises dispersing active agent particles in a liquid dispersion media in which the active agent is poorly soluble, followed by applying mechanical means in the presence of grinding media to reduce the particle size of the active agent to the desired effective average particle size. The dispersion media can be, for example, water, safflower oil, ethanol, t-butanol, glycerin, polyethylene glycol (PEG), hexane, or glycol. Water is a preferred dispersion media.

The active agent particles are preferably reduced in size in the presence of at least one peptide surface stabilizer. Alternatively, the active agent particles can be contacted with at least one peptide surface stabilizer either during or after attrition. One or more secondary surface stabilizers may also be added before, during, or after attrition. Other compounds, such as a diluent, can be added to the active agent/peptide surface stabilizer composition before, during, or after the size reduction process. Dispersions can be manufactured continuously or in a batch mode.

2. Precipitation to Obtain Nanoparticulate Active Agent Compositions

Another method of forming the desired nanoparticulate active agent composition is by microprecipitation. This is a method of preparing stable dispersions of poorly soluble active agents in the presence of one or more peptide surface stabilizers and one or more colloid stability enhancing surface active agents free of any trace toxic solvents or solubilized heavy metal impurities. Such a method comprises, for example: (1) dissolving the poorly soluble active agent in a suitable solvent; (2) adding the formulation from step (1) to a solution comprising at least one peptide surface stabilizer and optionally one or more secondary surface stabilizers, to form a clear solution; and (3) precipitating the formulation from step (2) using an appropriate non-solvent. The method can be followed by removal of any formed salt, if present, by dialysis or diafiltration and concentration of the dispersion by conventional means.

3. Homogenization to Obtain Nanoparticulate Active Agent Compositions

Exemplary homogenization methods of preparing active agent nanoparticulate compositions are described in U.S. Pat. No. 5,510,118, for "Process of Preparing Therapeutic Compositions Containing Nanoparticles."

Such a method comprises dispersing active agent particles in a liquid dispersion media in which the active agent is poorly soluble, followed by subjecting the dispersion to homogenization to reduce the particle size of the active agent to the desired effective average particle size. The active agent particles can be reduced in size in the presence of at least one peptide surface stabilizer and, if desired, one or more additional surface stabilizers. Alternatively, the active agent particles can be contacted with at least one peptide surface stabilizer and, if desired, one or more additional surface stabilizers, either during or after attrition. Other compounds, such as a diluent, can be added to the active agent/peptide surface stabilizer composition either before, during, or after the size reduction process. Dispersions can be manufactured continuously or in a batch mode.

C. Methods of Using Nanoparticulate Active Agent Formulations

The nanoparticulate active agent compositions of the present invention can be administered to humans and animals via any conventional means including, but not limited to, orally, rectally, ocularly, parenterally (intravenous, intramuscular, or subcutaneous), intracisternally, pulmonary, intravaginally, intraperitoneally, locally (powders, ointments or drops), or as a buccal or nasal spray.

Compositions suitable for parenteral injection may comprise physiologically acceptable sterile aqueous or nonaqueous solutions, dispersions, suspensions or emulsions and sterile powders for reconstitution into sterile injectable solutions or dispersions. Examples of suitable aqueous and nonaqueous carriers, diluents, solvents, or vehicles including water, ethanol, polyols (propyleneglycol, polyethylene-glycol, glycerol, and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions, and by the use of surfactants.

The nanoparticulate active agent compositions may also contain adjuvants such as preserving, wetting, emulsifying, and dispensing agents. Prevention of the growth of microorganisms can be ensured by various antibacterial and antifungal agents, such as parabens, chlorobutanol, phenol, sorbic acid, and the like. It may also be desirable to include isotonic agents, such as sugars, sodium chloride, and the like. Prolonged absorption of the injectable pharmaceutical form can be brought about by the use of agents delaying absorption, such as aluminum monostearate and gelatin.

Solid dosage forms for oral administration include capsules, tablets, pills, powders, and granules. In such solid dosage forms, the active agent is admixed with at least one of the following: (a) one or more inert excipients (or carrier), such as sodium citrate or dicalcium phosphate; (b) fillers or extenders, such as starches, lactose, sucrose, glucose, mannitol, and silicic acid; (c) binders, such as carboxymethylcellulose, alignates, gelatin, polyvinylpyrrolidone, sucrose and acacia; (d) humectants, such as glycerol; (e) disintegrating agents, such as agar-agar, calcium carbonate, potato or tapioca starch, alginic acid, certain complex silicates, and sodium carbonate; (f) solution retarders, such as paraffin; (g) absorption accelerators, such as quaternary ammonium compounds; (h) wetting agents, such as cetyl alcohol and glycerol monostearate; (i) adsorbents, such as kaolin and bentonite; and (j) lubricants, such as talc, calcium stearate, magnesium stearate, solid polyethylene glycols, sodium lauryl sulfate, or mixtures thereof. For capsules, tablets, and pills, the dosage forms may also comprise buffering agents.

Liquid dosage forms for oral administration include pharmaceutically acceptable emulsions, solutions, suspensions, syrups, and elixirs. In addition to the active agent, the liquid dosage forms may comprise inert diluents commonly used in the art, such as water or other solvents, solubilizing agents, and emulsifiers. Exemplary emulsifiers are ethyl alcohol, isopropyl alcohol, ethyl carbonate, ethyl acetate, benzyl alcohol, benzyl benzoate, propyleneglycol, 1,3-butyleneglycol, dimethylformamide, oils, such as cottonseed oil, groundnut oil, corn germ oil, olive oil, castor oil, and sesame oil, glycerol, tetrahydrofurfuryl alcohol, polyethyleneglycols, fatty acid esters of sorbitan, or mixtures of these substances, and the like.

Besides such inert diluents, the composition can also include adjuvants, such as wetting agents, emulsifying and suspending agents, sweetening, flavoring, and perfuming agents.

Actual dosage levels of active agent in the nanoparticulate compositions of the invention may be varied to obtain an amount of active agent that is effective to obtain a desired therapeutic response for a particular composition and method of administration. The selected dosage level therefore depends upon the desired therapeutic effect, the route of administration, the potency of the administered active agent, the desired duration of treatment, and other factors.

Dosage unit compositions may contain such amounts of such submultiples thereof as may be used to make up the daily dose. It will be understood, however, that the specific dose level for any particular patient will depend upon a variety of factors including the body weight, general health, sex, diet, time and route of administration, potency of the administered active agent, rates of absorption and excretion, combination with other active agents, and the severity of the particular disease being treated.

The following examples are given to illustrate the present invention. It should be understood, however, that the invention is not to be limited to the specific conditions or details described in these examples. Throughout the specification, any and all references to a publicly available document, including a U.S. patent, are specifically incorporated by reference.

The formulations in the examples that follow were also investigated using a light microscope. Here, "stable" nanoparticulate dispersions (uniform Brownian motion) were readily distinguishable from "aggregated" dispersions (relatively large, nonuniform particles without motion).

Example 1

The purpose of this example was to prepare a nanoparticulate nystatin composition having a peptide surface stabilizer.

Nystatin is a poorly water-soluble antimycotic polyene antibiotic obtained from *Streptomyces noursei*. It is an antifungal agent indicated for oral, gastrointestinal, and vaginal candidiasis. Oral candidiasis, in particular, is a common affliction of immunocompromised patients. Nystatin is indicated in the therapy of all infections caused by susceptible microorganisms in those patients in whom candidal (monilial) infections are most likely to complicate therapy.

A slurry of 2% (w/w) nystatin (Sigma-Aldrich Co.) and 1% (w/w) poly(Lysine, Tryptophan) 4:1 hydrobromide ("Poly (Lys,Trp)") (Sigma; St. Louis, Mo.), which is a cationic random co-polyamino acid having a molecular weight of 38,000, in water was milled for 1 day using low energy (ball milling) techniques in the presence of ceramic YTZ grinding media.

The mean size of the nystatin particles following milling was 149 nm, with a D90 of 270 nm, as determined by static light scattering using a Horiba LA-910 light-scattering particle size analyzer (Horiba Instruments, Irvine, Calif.). The composition had a zeta potential of 47.7 mV, as measured by electrophoresis in $5 \times 10^{-4}$ M NaCl (Malvern ZetaSizer). Dispersibility was verified by phase contrast microscopy.

FIG. 1 shows representative photomicrographs of the nystatin crystals before (FIG. 1A) and after (FIG. 1B) milling.

Figure 2:
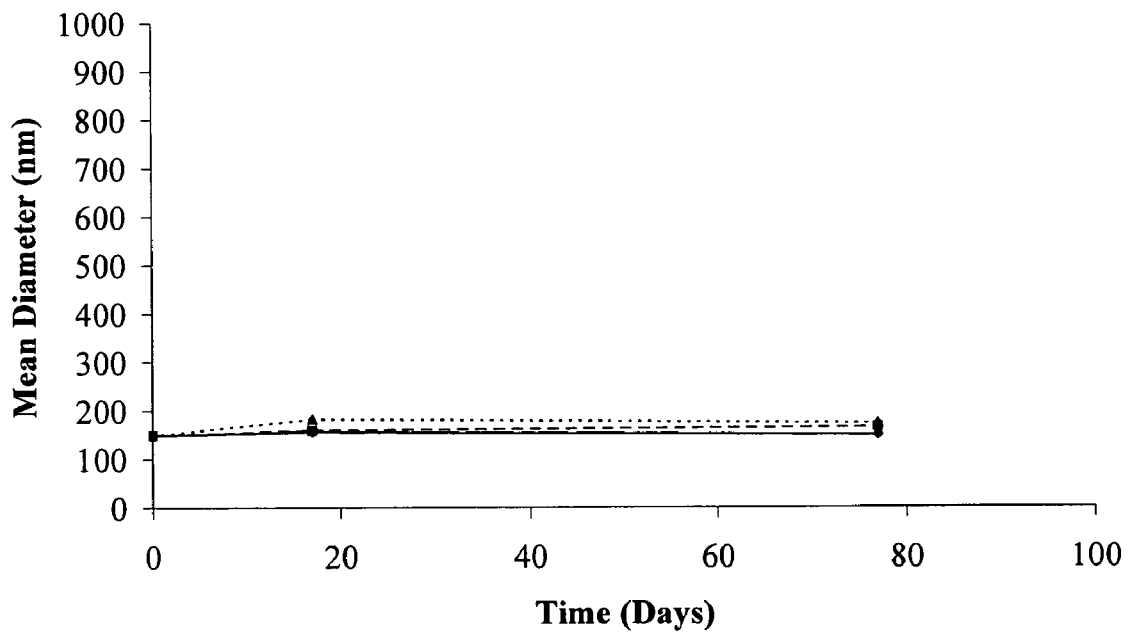
FIG. 2: Shows the results of monitoring the particle size stability over time at 5° C. (solid line), 25° C. (dashed line), and 40° C. (dotted line) for a nanoparticulate nystatin composition comprising the peptide poly(Lysine, Tryptophan) 4:1 hydrobromide as a surface stabilizer.

Particle size stability under controlled conditions was monitored over time. FIG. 2 shows the results of monitoring the nystatin particle size stability over time at 5° C. (solid line), 25° C. (dashed line), and 40° C. (dotted line) for the nanoparticulate nystatin/peptide composition.

These results demonstrate that a peptide surface stabilizer can be successfully used to stabilize an active agent at a nanoparticulate particle size. Moreover, such a peptide surface stabilizer may confer additional therapeutic advantages to the final formulation. For example, the peptide surface stabilizer Poly(Lys,Trp) is cationic and, therefore, nanoparticulate active agent compositions utilizing this surface stabilizer will be bioadhesive.

The resultant composition exhibited a mean particle sizes of 149 nm and were free of agglomeration. Moreover, the nanoparticulate nystatin/peptide composition exhibited virtually no particle size growth at all three temperatures tested.

Example 2

The purpose of this example was to determine whether a cationic surface charge, such as that obtained with the use of a cationic peptide surface stabilizer, enhances the adhesion of small particles to cells.

Cell-binding experiments were performed with polystyrene latex microspheres as a model. A positive surface charge would be expected to enhance the interaction of particles with cell-surface macromolecules, which have a net negative charge.

Cationic microspheres with a mean zeta-potential (51.5 mV) comparable to the nanoparticulate nystatin/peptide composition of Example 1 were tested against anionic microspheres (mean zeta-potential=−50.9 mV). The microspheres were incubated with NIH/3T3 fibroblasts, washed thoroughly, fixed, and subjected to SEM analysis.

Figure 3:
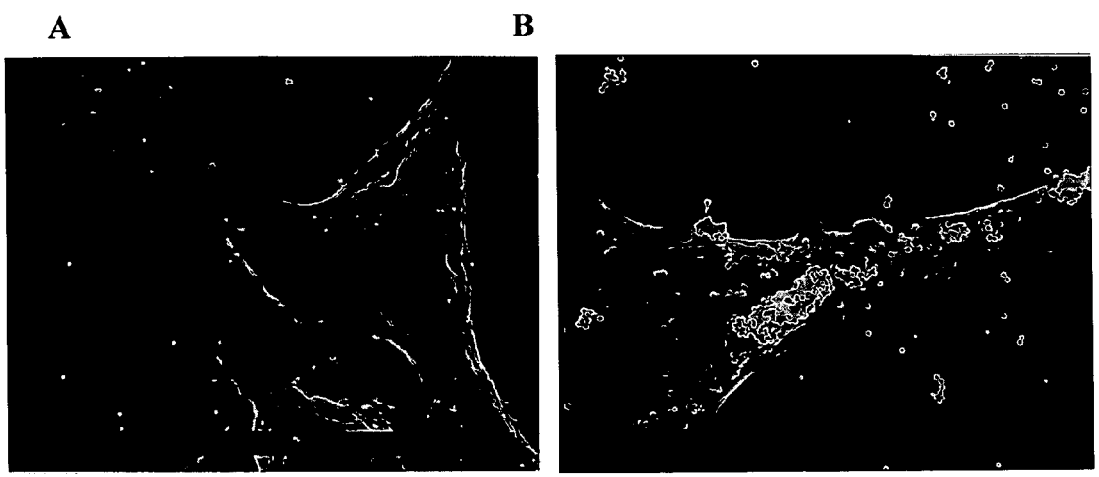
FIG. 3: Shows representative micrographs of cells with anionic particles (FIG. 3A) and cationic particles (FIG. 3B).

FIG. 3 shows representative micrographs of cells with anionic particles (FIG. 3A) and cationic particles (FIG. 3B).

The results indicate that positively-charged particles interact more strongly with the cell surface than negatively-charged particles, and it is believed that nanoparticulate active agent compositions having a cationic peptide as a surface stabilizer with comparable zeta potentials will follow the same trend.

Example 3

The purpose of this example was to determine if milling of an active agent, such as nystatin, having a peptide surface stabilizer affects the active agent's activity.

The minimum inhibitory concentration (MIC) of a milled nystatin composition having as a peptide surface stabilizer Poly(Lys, Trp) was compared to the MIC of two unmilled nystatin compositions. Nystatin for the milled nanoparticulate composition was obtained from Sigma-Aldrich Co. and the two unmilled nystatin compositions were obtained from Sigma-Aldrich Co. and Paddock Laboratories, Inc. Details regarding the milled and unmilled nystatin compositions are given in Table 1 below, including particle size of the milled nanoparticulate nystatin/Poly(Lys, Trp) composition and the potency (USP U/ml) and MIC for each nystatin composition.

TABLE 1

| Nystatin Concentration | Surface Stabilizer and Concentration | Mean Particle Size (nm) | Potency (USP U/ml) | MIC |
|---|---|---|---|---|
| 2% (Sigma) | 1% Poly(Lys, Trp)[1] | 129 | 101,200 | 1:10,000 |
| 5% (Sigma) | N/A - unmilled | N/A | 253,000 | 1:10,000 |
| 4% (Paddock) | N/A - unmilled | N/A | 253,000 | 1:100,000 |

[1]Poly(Lysine, Tryptophan) is a cationic random co-polyamino acid.

The nanoparticulate sample was ball milled for 26 hours with ceramic YTZ milling media.

The minimum inhibitory concentration (MIC) of the milled nystatin/peptide composition and the two unmilled samples were determined in cultures of *C. albicans*. MIC as reported here is the maximum dilution of formulation in culture broth which inhibits growth of *C. albicans*. As shown in Table 1, above, the milled nystatin/peptide composition did not exhibit any significant differences in MIC, and surprisingly, was more active than at least one of the unmilled nystatin samples. These data confirm that the milling process does not decrease the activity of nystatin.

Example 4

The purpose of this example was to prepare a nanoparticulate composition of a diuretic, Compound A, utilizing a peptide surface stabilizer. Diuretics can be used to reduce the swelling and fluid retention caused by various medical problems, including heart or liver disease. They are also is used to treat high blood pressure.

A slurry of 2% (w/w) Compound A and 1% (w/w) poly (Lysine, Tryptophan) 4:1 hydrobromide as a peptide surface stabilizer in water was milled for 3 days in an aqueous environment in a low energy mill, in the presence of 0.8 mm yttrium-stabilized ceramic media.

Particle size analysis of the resulting Compound A dispersion was conducted via laser light diffraction using the Horiba LA 910 particle size analyzer (Horiba Instruments, Irvine, Calif.) and water as a diluent. The mean particle size of the milled Compound A dispersion was 99 nm, with a D90 of 138 nm. The composition was stable.

Example 5

The purpose of this example was to prepare a nanoparticulate composition of paclitaxel utilizing a peptide surface stabilizer. Paclitaxel belongs to the group of medicines called antineoplastics. It is used to treat cancer of the ovaries, breast, certain types of lung cancer, and a cancer of the skin and mucous membranes more commonly found in patients with acquired immunodeficiency syndrome (AIDS). It may also be used to treat other kinds of cancer.

Paclitaxel has the following chemical structure:

A slurry of 2% (w/w) paclitaxel and 1% (w/w) poly(L-ysine, Tryptophan) 4:1 hydrobromide as a peptide surface stabilizer in water was milled for 3 days in an aqueous environment in a low energy mill, in the presence of 0.8 mm yttrium-stabilized ceramic media.

Particle size analysis of the resulting paclitaxel dispersion was conducted via laser light diffraction using the Horiba LA 910 particle size analyzer (Horiba Instruments, Irvine, Calif.) and water as a diluent. The mean particle size of the milled paclitaxel dispersion was 139 nm, with a D90 of 185 nm. The composition was stable.

Example 6

The purpose of this example was to prepare a nanoparticulate composition of amphotericin B utilizing a peptide surface stabilizer. Amphotericin B is a poorly water soluble antifungal agent. Topically, it is used to treat skin yeast infections; intravenously, it is used to treat a variety of life-threatening fungal infections.

Amphotericin B has the following chemical structure:

In this experiment, amphotericin B was milled with Poly (Lys, Trp) 4:1 Hydrobromide as a peptide surface stabilizer. A 2% (w/w) slurry of amphotericin B (Sigma) in water was prepared with 1% (w/w) poly (Lys, Trp) (Sigma). The composition was ball-milled for 24 hours with 0.8 mm ceramic YTZ milling media. The particle size of the resulting amphotericin B dispersion was characterized by static laser light scattering on a Horiba LA-910 particle size distribution analyzer. The results are shown in Table 2, below.

TABLE 2

| Drug and Concentration | Surface Stabilizer and Concentration | Mean Particle Size (nm) | D50 (nm) | D90 (nm) |
|---|---|---|---|---|
| 2% Amphotericin B | 1% Poly(Lys, Trp) | 121 | 96 | 230 |

These results demonstrate that amphotericin B dispersions can be successfully stabilized by a peptide surface stabilizer, such as the random copolypeptide poly (Lys, Trp) 4:1 Hydrobromide.

It will be apparent to those skilled in the art that various modifications and variations can be made in the methods and compositions of the present invention without departing from the spirit or scope of the invention. Thus, it is intended that the present invention cover the modifications and variations of this invention provided they come within the scope of the appended claims and their equivalents.

We claim:

1. A composition comprising:
   (a) particles of at least one active agent having an effective average particle size of less than about 2000 nm; and
   (b) at least one water soluble peptide surface stabilizer adsorbed on the surface of the active agent,
   wherein the peptide surface stabilizer is poly(Lysine, Tryptophan) 4:1 hydrobromide wherein:
   (a) the active agent is present in an amount selected from the group consisting of from about 99.5% to about 0.001%, from about 95% to about 0.1%, and from about 90% to about 0.5%, by weight, based on the total combined dry weight of the active agent and at least one peptide surface stabilizer, not including other excipients; or
   (b) the at least one surface stabilizer is present in an amount selected from the group consisting of from about 0.5% to about 99.999% by weight, from about 5.0% to about 99.9% by weight, and from about 10% to about 99.5% by weight, based on the total combined dry weight of the active agent and at least one peptide surface stabilizer, not including other excipients, and wherein the composition does not produce significantly different absorption levels when administered under fed as compared to fasting conditions.

2. The composition of claim 1, further comprising at least one secondary surface stabilizer.

3. The composition of claim 2, wherein the secondary surface stabilizer is selected from the group consisting of an anionic surface stabilizer, a cationic surface stabilizer, a zwitterionic surface stabilizer, a non-ionic surface stabilizer, and an ionic surface stabilizer.

4. The composition of claim 2, wherein the secondary surface stabilizer is selected from the group consisting of cetyl pyridinium chloride, dextran, glycerol, gum acacia, cholesterol, tragacanth, stearic acid, benzalkonium chloride, calcium stearate, glycerol monostearate, cetostearyl alcohol, cetomacrogol emulsifying wax, sorbitan esters, polyoxyethylene alkyl ethers, polyoxyethylene castor oil derivatives, polyoxyethylene sorbitan fatty acid esters, polyethylene glycols, dodecyl trimethyl ammonium bromide, polyoxyethylene stearates, colloidal silicon dioxide, phosphates, sodium dodecylsulfate, carboxymethylcellulose calcium, hydroxypropyl celluloses, hypromellose, carboxymethylcellulose sodium, methylcellulose, hydroxyethylcellulose, hypromellose phthalate, noncrystalline cellulose, magnesium aluminum silicate, triethanolamine, polyvinyl alcohol, polyvinylpyrrolidone, 4-(1, 1,3,3-tetramethylbutyl)-phenol polymer with ethylene oxide and formaldehyde, poloxamers; poloxamines, a charged phospholipid, dioctylsulfosuccinate, dialkylesters of sodium sulfosuccinic acid, sodium lauryl sulfate, alkyl aryl polyether sulfonates, mixtures of sucrose stearate and sucrose distearate, p-isononylphenoxypoly-(glycidol), decanoyl-N-methylglucamide; n-decyl β-D-glucopyranoside; n-decyl β-D-maltopyranoside; n-dodecyl β-D-glucopyranoside; n-dodecyl β-D-maltoside; heptanoyl-N-methylglucamide; n-heptyl-β-D-glucopyranoside; n-heptyl β-D-thioglucoside; n-hexyl β-D-glucopyranoside; nonanoyl-N-methylglucamide; n-noyl β-D-glucopyranoside; octanoyl-N-methylglucamide; n-octyl-β-D-glucopyranoside; octyl β-D-thioglucopyranoside; PEG-phospholipid, PEG-cholesterol, PEG-cholesterol derivative, PEG-vitamin A, random copolymers of vinyl acetate and vinyl pyrrolidone, a cationic polymer, a cationic biopolymer, a cationic polysaccharide, a cationic cellulosic, a cationic alginate, a cationic nonpolymeric compound, a cationic phospholipids, cationic lipids, polymethylmethacrylate trimethylammonium bromide, sulfonium compounds, polyvinylpyrrolidone-2-dimethylaminoethyl methacrylate dimethyl sulfate, hexadecyltrimethyl ammonium bromide, phosphonium compounds, quarternary ammonium compounds, benzyl-di(2-chloroethyl)ethylammonium bromide, coconut trimethyl ammonium chloride, coconut trimethyl ammonium bromide, coconut methyl dihydroxyethyl ammonium chloride, coconut methyl dihydroxyethyl ammonium bromide, decyl triethyl ammonium chloride, decyl dimethyl hydroxyethyl ammonium chloride, decyl dimethyl hydroxyethyl ammonium chloride bromide, $C_{12-15}$dimethyl hydroxyethyl ammonium chloride, $C_{12-15}$dimethyl hydroxyethyl ammonium chloride bromide, coconut dimethyl hydroxyethyl ammonium chloride, coconut dimethyl hydroxyethyl ammonium bromide, myristyl trimethyl ammonium methyl sulphate, lauryl dimethyl benzyl ammonium chloride, lauryl dimethyl benzyl ammonium bromide, lauryl dimethyl (ethenoxy)$_4$ ammonium chloride, lauryl dimethyl (ethenoxy)$_4$ ammonium bromide, N-alkyl $(C_{12-18})$dimethylbenzyl ammonium chloride, N-alkyl $(C_{14-18})$dimethyl-benzyl ammonium chloride, N-tetradecylidimethylbenzyl ammonium chloride monohydrate, dimethyl didecyl ammonium chloride, N-alkyl and $(C_{12-14})$ dimethyl 1-napthylmethyl ammonium chloride, trimethylammonium halide, alkyl-trimethylammonium salts, dialkyl-dimethylammonium salts, lauryl trimethyl ammonium chloride, ethoxylated alkyamidoalkyldialkylammonium salt, an ethoxylated trialkyl ammonium salt, dialkylbenzene dialkylammonium chloride, N-didecyldimethyl ammonium chloride, N-tetradecyldimethylbenzyl ammonium, chloride monohydrate, N-alkyl$(C_{12-14})$ dimethyl 1-naphthylmethyl ammonium chloride, dodecyldimethylbenzyl ammonium chloride, dialkyl benzenealkyl ammonium chloride, lauryl trimethyl ammonium chloride, alkylbenzyl methyl ammonium chloride, alkyl benzyl dimethyl ammonium bromide, $C_{12}$ trimethyl ammonium bromides, $C_{15}$ trimethyl ammonium bromides, $C_{17}$ trimethyl ammonium bromides, dodecylbenzyl triethyl ammonium chloride, poly-diallyldimethylammonium chloride (DADMAC), dimethyl ammonium chlorides, alkyldimethylammonium halogenides, tricetyl methyl ammonium chloride, decyltrimethylammonium bromide, dodecyltriethylammonium bromide, tetradecyltrimethylammonium bromide, methyl trioctylammonium chloride, polyquaternium 10, tetrabutylammonium bromide, benzyl trimethylammonium bromide, choline esters, benzalkonium chloride, stearalkonium chloride compounds, cetyl pyridinium bromide, cetyl pyridinium chloride, halide salts of quaternized polyoxyethylalkylamines, quaternized ammonium salt polymers, alkyl pyridinium salts; amines, amine salts, amine oxides, imide azolinium salts, protonated quaternary acrylamides, methylated quaternary polymers, and cationic guar.

5. The composition of claim 1, wherein the composition is formulated for administration selected from the group consisting of oral, pulmonary, rectal, opthalmic, colonic, parenteral, intracisternal, intravaginal, intraperitoneal, local, buccal, nasal, and topical administration.

6. The composition of claim 1 formulated into a dosage form selected from the group consisting of liquid dispersions, oral suspensions, gels, aerosols, ointments, creams, tablets, capsules, sachets, lozenges, powders, pills, granules, controlled release formulations, fast melt formulations, lyophilized formulations, delayed release formulations, extended release formulations, pulsatile release formulations, and mixed immediate release and controlled release formulations.

7. The composition of claim 1 further comprising one or more pharmaceutically acceptable excipients, carriers, or a combination thereof.

8. The composition of claim 1, wherein the active agent is selected from the group consisting of a crystalline phase, an amorphous phase, and a semi-crystalline phase.

9. The composition of claim 1, wherein the effective average particle size of the active agent particles is selected from the group consisting of less than about 1900 nm, less than about 1800 nm, less than about 1700 nm, less than about 1600 nm, less than about 1500 nm, less than about 1400 nm, less than about 1300 nm, less than about 1200 nm, less than about 1100 nm, less than about 1000 nm, less than about 900 nm, less than about 800 nm, less than about 700 nm, less than about 600 nm, less than about 500 nm, less than about 400 nm, less than about 300 nm, less than about 250 nm, less than about 200 nm, less than about 100 nm, less than about 75 nm, and less than about 50 nm.

10. The composition of claim 9, wherein at least about 70%, at least about 90%, at least about 95%, or at least about 99% of the active agent particles have a particle size less than the effective average particle size.

11. The composition of claim 1, further comprising at least one additional active agent composition having an effective average particle size which is different that the effective average particle size of the active agent composition of claim 1.

12. The composition of claim 1, wherein the active agent is selected from the group consisting of nystatin, paclitaxel, amphotericin B, a diuretic, a dermal agent, nutraceuticals, COX-2 inhibitors, retinoids, anticancer agents, NSAIDS, proteins, peptides, nucleotides, anti-obesity drugs, dietary supplements, carotenoids, corticosteroids, elastase inhibitors, anti-fungals, oncology therapies, anti-emetics, analgesics, cardiovascular agents, anti-inflammatory agents, anthelmintics, anti-arrhythmic agents, antibiotics, anticoagulants, antidepressants, antidiabetic agents, antiepileptics, antihistamines, antihypertensive agents, antimuscarinic agents, antimycobacterial agents, antineoplastic agents, immunosuppressants, antithyroid agents, antiviral agents, anxiolytics, sedatives, astringents, beta-adrenoceptor blocking agents, blood products and substitutes, cardiac inotropic agents, contrast media, corticosteroids, cough suppressants, diagnostic agents, diagnostic imaging agents, diuretics, dopaminergics, haemostatics, immunological agents, lipid regulating agents, muscle relaxants, parasympathomimetics, parathyroid calcitonin, parathyroid biphosphonates, prostaglandins, radiopharmaceuticals, sex hormones, anti-allergic agents, stimulants, anoretics, sympathomimetics, thyroid agents, vasodilators, xanthines, acyclovir, alprazolam, altretamine, amiloride, amiodarone, benztropine mesylate, bupropion, cabergoline, candesartan, cerivastatin, chlorpromazine, ciprofloxacin, cisapride, clarithromycin, clonidine, clopidogrel, cyclobenzaprine, cyproheptadine, delavirdine, desmopressin, diltiazem, dipyridamole, dolasetron, enalapril maleate, enalaprilat, famotidine, felodipine, furazolidone, glipizide, irbesartan, ketoconazole, lansoprazole, loratadine, loxapine, mebendazole, mercaptopurine, milrinone lactate, minocycline, mitoxantrone, nelfinavir mesylate, nimodipine, norfloxacin, olanzapine, omeprazole, penciclovir, pimozide, tacolimus, quazepam, raloxifene, rifabutin, rifampin, risperidone, rizatriptan, saquinavir, sertraline, sildenafil, acetylsulfisoxazole, temazepam, thiabendazole, thioguanine, trandolapril, triamterene, trimetrexate, troglitazone, trovafloxacin, verapamil, vinblastine sulfate, mycophenolate, atovaquone, atovaquone, proguanil, ceftazidime, cefuroxime, etoposide, terbinafine, thalidomide, fluconazole, amsacrine, dacarbazine, teniposide, and acetylsalicylate.

13. The composition of claim 12, wherein the nutraceutical is selected from the group consisting of dietary supplements, vitamins, minerals, herbs, lutein, folic acid, fatty acids, fruit extracts, vegetable extracts, phosphatidylserine, lipoic acid, melatonin, glucosamine/chondroitin, Aloe Vera, Guggul, glutamine, amino acids, green tea, lycopene, whole foods, food additives, herbs, phytonutrients, antioxidants, flavonoid constituents of fruits, evening primrose oil, flax seeds, fish oils, marine animal oils, and probiotics.

14. The composition of claim 12, wherein the anticancer agent is selected from the group consisting of alkylating agents, antimetabolites, anthracenediones, natural products, hormones, antagonists, radiosensitizers, platinum coordination complexes, adrenocortical suppressants, immunosuppressive agent, substituted ureas, and COX-2 inhibitors.

15. The composition of claim 14, wherein:
(a) the alkylating agent is selected from the group consisting of chlormethine, chlorambucile, melphalan, uramustine, mannomustine, extramustinephoshate, mechlore-thaminoxide, cyclophosphamide, ifosfamide, trifosfamide, tretamine, thiotepa, triaziquone, mitomycine, busulfan, piposulfan, piposulfam, carmustine, lomustine, semustine, streptozotocine, mitobronitole, dacarbazine and procarbazine; or (b) the antimetabolite is selected from the group consisting of methotrexate, fluorouracil, floxuridine, tegafur, cytarabine, idoxuridine, flucytosine, mercaptopurine, thioguanine, azathioprine, tiamiprine, vidarabine, pentostatin, and puromycine; or (c) the natural product is selected from the group consisting of vinblastine, vincristine, etoposide, teniposide, adriamycine, daunomycine, doctinomycin, daunorubicin, doxorubicin, mithramycin, bleomycin, mitomycin, L-asparaginase, alpha-interferon, camptothecin, taxol, and retinoic acid; or (d) the hormone or antagonist is selected from the group consisting of prednisone, hydroxyprogesterone caproate, medroxyprogesterone acetate, megestrol acetate, diethylstilbestrol, ethinyl estradiol, tamoxifen, testosterone propionate, fluoxymesterone, flutamide, leuprolide; or (e) the anticancer agent is selected from the group consisting of cisplatin, carboplatin, mitoxantrone, hydroxyurea, mitotane, aminoglutethimide, cyclosporine, azathioprine, sulfasalazine, methoxsalen, and thalidomide.

16. The composition of claim 12, wherein the NSAID is selected from the group consisting of nabumetone, tiaramide, proquazone, bufexamac, flumizole, epirazole, tinoridine, timegadine, dapsone, aspirin, diflunisal, benorylate, fosfosal, diclofenac, alclofenac, fenclofenac, etodolac, indomethacin, sulindac, tolmetin, fentiazac, tilomisole, carprofen, fenbufen, flurbiprofen, ketoprofen, oxaprozin, suprofen, tiaprofenic acid, ibuprofen, naproxen, fenoprofen, indoprofen, pirprofen, flufenamic, mefenamic, meclofenamic, niflumic, oxyphenbutazone, phenylbutazone, apazone, feprazone, piroxicam, sudoxicam, isoxicam, and tenoxicam.

17. The composition of claim 12, wherein the COX-2 inhibitor is selected from the group consisting of nimesulide, celecoxib, rofecoxib, meloxicam, valdecoxib, parecoxib, etoricoxib, flurbiprofen, nabumetone, etodolac, iguratimod, flosulide, piroxicam, diclofenac, lumiracoxib, monteleukast, pranlukast, heptinylsulfide, SC-236, SC-58125, SC-57666, SC-558, SC-560, SC 41930, NS-398, DFU, L-745337, L-761066, L-761000, L-748780, DUP-697, PGV 20229, BF 389, CL 1004, PD 136005, PD 142893, PD 138387, PD 145065, D 1367, R 807, JTE-522, FK-3311, FK 867, FR 140423, FR 115068, GR 253035, RWJ 63556, RWJ 20485, ZK 38997, S 2474, RS 57067, RS 104897, RS 104894, and SB 209670.

18. The composition of claim 1, wherein upon administration to a mammal the active agent particles redisperse such that the particles have an effective average particle size selected from the group consisting of less than about 2 microns, less than about 1900 nm, less than about 1800 nm, less than about 1700 nm, less than about 1600 nm, less than about 1500 nm, less than about 1400 nm, less than about 1300 nm, less than about 1200 nm, less than about 1100 nm, less than about 1000 nm, less than about 900 nm, less than about 800 nm, less than about 700 nm, less than about 600 nm, less than about 500 nm, less than about 400 nm, less than about 300 nm, less than about 250 nm, less than about 200 nm, less than about 150 nm, less than about 100 nm, less than about 75 nm, and less than about 50 nm.

19. The composition of claim 1, wherein the composition redisperses in a biorelevant media such that the active agent particles have an effective average particle size selected from the group consisting of less than about 2 microns, less than about 1900 nm, less than about 1800 nm, less than about 1700 nm, less than about 1600 nm, less than about 1500 nm, less than about 1400 nm, less than about 1300 nm, less than about 1200 nm, less than about 1100 nm, less than about 1000 nm, less than about 900 nm, less than about 800 nm, less than about 700 nm, less than about 600 nm, less than about 500 nm, less than about 400 nm, less than about 300 nm, less than about 250 nm, less than about 200 nm, less than about 150 nm, less than about 100 nm, less than about 75 nm, and less than about 50 nm.

20. The composition of claim 19, wherein the biorelevant media is selected from the group consisting of water, aqueous electrolyte solutions, aqueous solutions of a salt, aqueous solutions of an acid, aqueous solutions of a base, and combinations thereof.

21. The composition of claim 1, wherein the difference in absorption of the active agent composition of the invention, when administered in the fed versus the fasted state, is selected from the group consisting of less than about 100%, less than about 90%, less than about 80%, less than about 70%, less than about 60%, less than about 50%, less than about 40%, less than about 30%, less than about 25%, less than about 20%, less than about 15%, less than about 10%, less than about 5%, and less than about 3%.

22. The composition of claim 1, wherein administration of the composition to a human in a fasted state is bioequivalent to administration of the composition to a subject in a fed state.

23. The composition of claim 22, wherein "bioequivalency" is established by:
    (a) a 90% Confidence Interval of between 0.80 and 1.25 for both $C_{max}$ and AUC; or
    (b) a 90% Confidence Interval of between 0.80 and 1.25 for AUC and a 90% Confidence Interval of between 0.70 to 1.43 for $C_{max}$.

24. A method of making a composition comprising contacting particles of at least one active agent with at least one water-soluble peptide surface stabilizer for a time and under conditions sufficient to provide an active agent composition having an effective average particle size of less than about 2000 nm and having the peptide surface stabilizer adsorbed on the surface of the active agent, wherein the peptide surface stabilizer is poly(Lysine, Tryptophan) 4:1 hydrobromide.

25. A method of treating a subject in need comprising administering a composition comprising:
    (a) particles of at least one active agent having an effective average particle size of less than about 2000 nm; and
    (b) at least one water soluble peptide surface stabilizer adsorbed on the surface of the active agent,
    wherein the peptide surface stabilizer is poly(Lysine, Tryptophan) 4:1 hydrobromide.

* * * * *